United States Patent
Young et al.

(10) Patent No.: US 10,130,417 B2
(45) Date of Patent: Nov. 20, 2018

(54) BIPOLAR ELECTROSURGICAL PROBE HAVING INSULATED OVERLAPPING CONDUCTIVE ELEMENTS

(75) Inventors: Kimbolt Young, Newtonville, MA (US); Rollie E. McCallister, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1255 days.

(21) Appl. No.: 13/563,437

(22) Filed: Jul. 31, 2012

(65) Prior Publication Data

US 2012/0296331 A1 Nov. 22, 2012

Related U.S. Application Data

(63) Continuation of application No. 12/262,073, filed on Oct. 30, 2008, now Pat. No. 8,241,281.

(60) Provisional application No. 60/985,201, filed on Nov. 3, 2007.

(51) Int. Cl.
*A61B 18/14* (2006.01)
*A61B 18/12* (2006.01)
*A61B 18/00* (2006.01)

(52) U.S. Cl.
CPC ...... *A61B 18/1477* (2013.01); *A61B 18/1206* (2013.01); *A61B 2018/00083* (2013.01)

(58) Field of Classification Search
CPC ............... A61B 18/1477; A61B 18/14; A61B 2018/126; A61B 2018/143; A61B 18/1206; A61B 2018/00083; A61B 2018/1402; A61B 2018/1405; A61B 2018/1465; A61B 2018/1467
USPC .............................................. 606/48, 41, 50
See application file for complete search history.

(56) References Cited

U.S. PATENT DOCUMENTS

| 3,920,021 | A | * | 11/1975 | Hiltebrandt | A61B 18/1442 606/50 |
| 4,590,950 | A | * | 5/1986 | Iwaszkiewicz | H01R 4/00 174/75 R |
| 6,723,094 | B1 | | 4/2004 | Desinger | |
| 6,922,579 | B2 | * | 7/2005 | Taimisto | A61B 18/1492 600/374 |
| 8,241,281 | B2 | | 8/2012 | Young et al. | |
| 2006/0047276 | A1 | | 3/2006 | Young et al. | |

(Continued)

OTHER PUBLICATIONS

PCT International Preliminary Report on Patentability (Chapter I of the Patent Cooperation Treaty) for PCT/US2008/081864, Applicant: Boston Scientific Scimed, Inc., Form PCT/IB/326 and 373, D dated May 14, 2010 (10 pages).

(Continued)

*Primary Examiner* — Kevin C Sirmons
*Assistant Examiner* — Leah Swanson
(74) *Attorney, Agent, or Firm* — Pauly, DeVries, Smith & Deffner LLC

(57) ABSTRACT

A bipolar electrosurgical probe configured for applying electrical energy to tissue includes a first tubular electrode carried by a probe shaft and having a distal end, a second tubular electrode carried by the probe shaft and having a proximal end, and an insulation member, wherein at least a portion of the insulation member is disposed between overlapping ends of the first and second tubular electrodes, wherein the distal end of the first electrode defines at least one aperture extending through a wall of the first electrode.

21 Claims, 29 Drawing Sheets

(56) References Cited

U.S. PATENT DOCUMENTS

| | | | |
|---|---|---|---|
| 2006/0100619 A1 | 5/2006 | McClurken et al. | |
| 2006/0206112 A1* | 9/2006 | Kasahara | A61B 1/042 |
| | | | 606/45 |
| 2009/0118731 A1 | 5/2009 | Young et al. | |

OTHER PUBLICATIONS

PCT Annex to Form PCT/ISAI206 Communication Relating to the Results of the Partial International Search dated 1 Mach 11, 2009 for International Application No. PCTIUS2008/081864, Applicant: Boston Scientific Scimed, Inc. (4 pages).
PCT Written Opinion of the International Search Authority for PCT/US2008-081864, Applicant: Boston Scientific Scimed, Inc., Form PCT/ISAI237, dated Jul. 20, 2009 (8 pages).
PCT International Search Report for PCT/US2008/081864, Applicant: Boston Scientific Scimed, Inc., Form PCTI ISAI21 0 and 220, dated Jul. 20, 2009 (8 pages).
"Communication Pursuant to Article 94(3) EPC," for European Patent Application No. 08845239.6 dated Feb. 13, 2014 (4 pages).
"Communication Pursuant to Article 94(3) EPC," for European Patent Application No. 08845239.6 dated Jul. 5, 2016 (5 pages).
"File History," for U.S. Appl. No. 12/262,073 (244 pages).
"Response to Communication Pursuant to Article 94(3) EPC," for European Patent Application No. 08845239.6 filed with the EPO Aug. 21, 2014 (3 pages).
"Response to Communication Pursuant to Article 94(3) EPC," for European Patent Application No. 08845239.6 filed with the EPO Jan. 13, 2017 (8 pages).

* cited by examiner

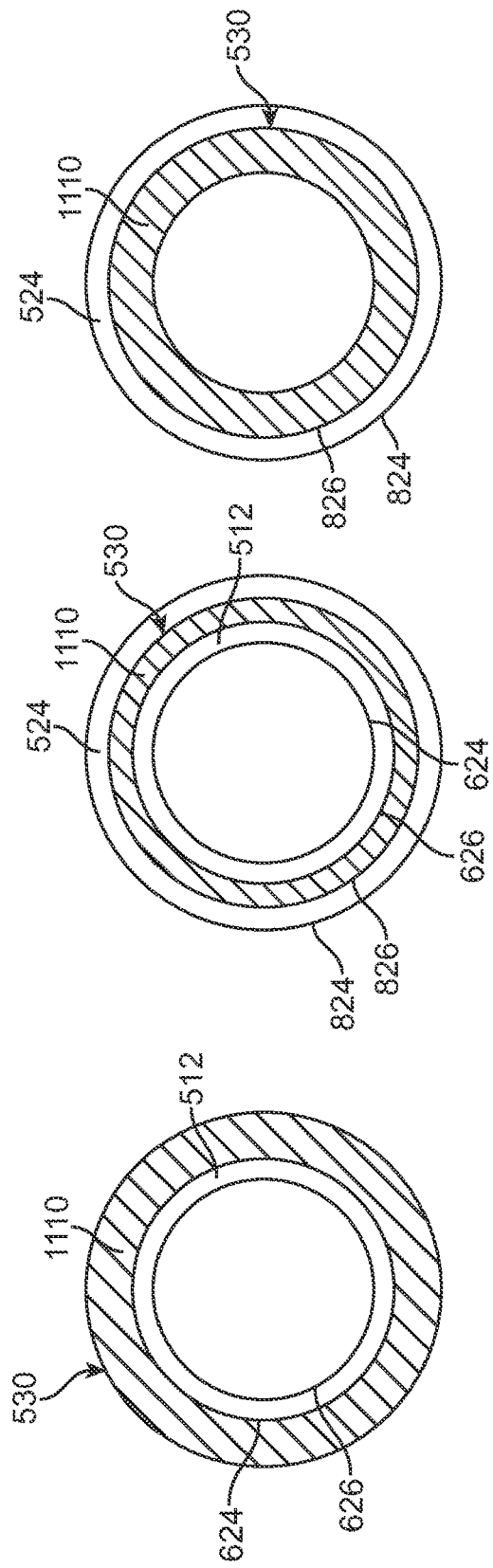

SECTION A-A

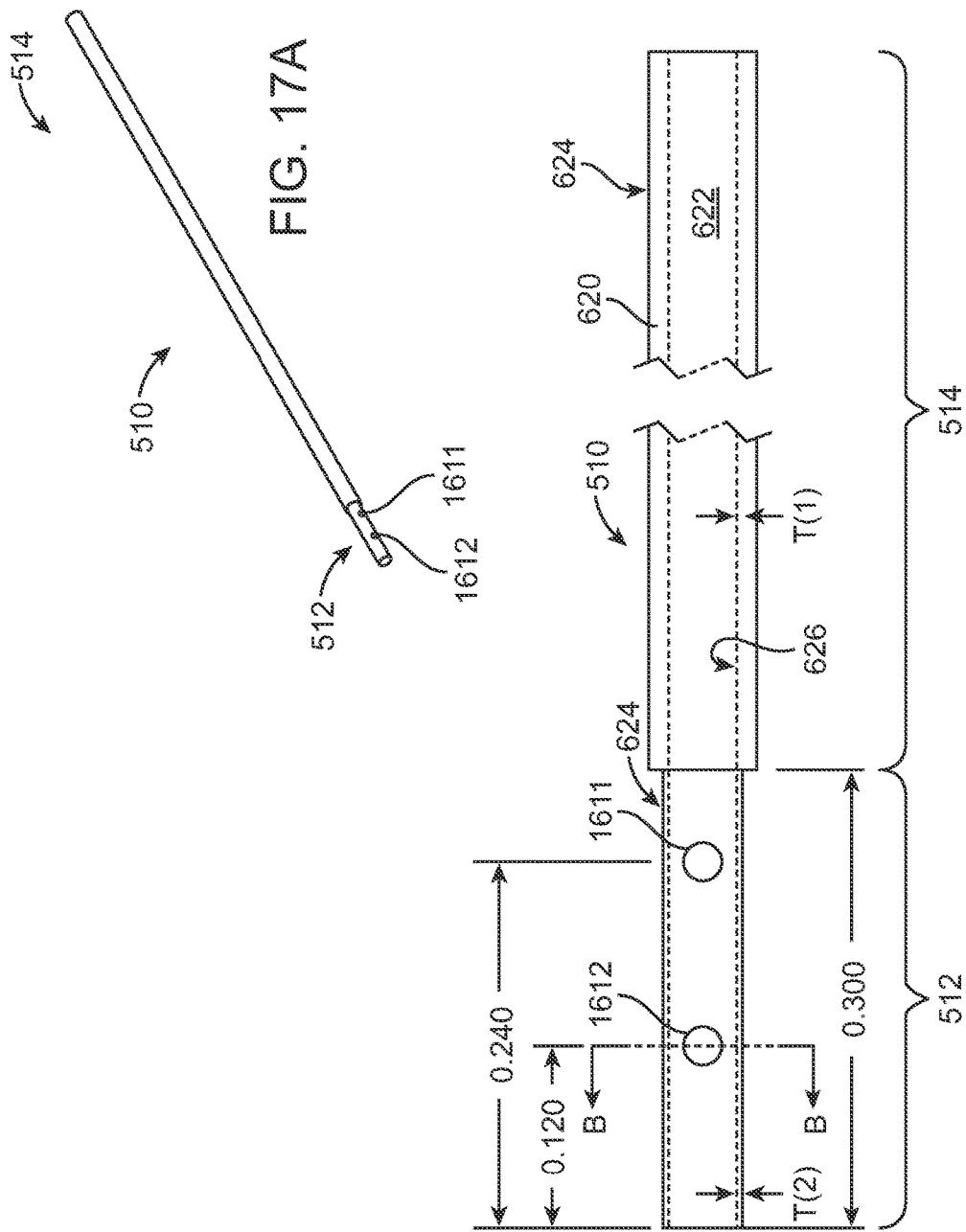

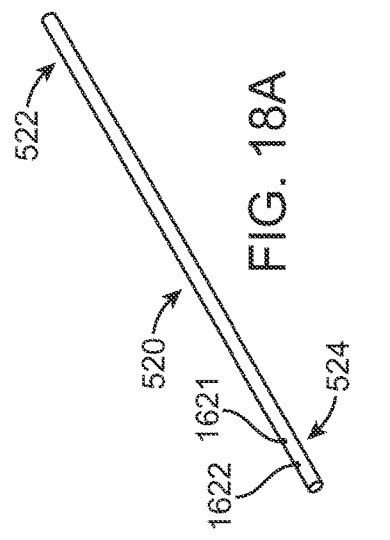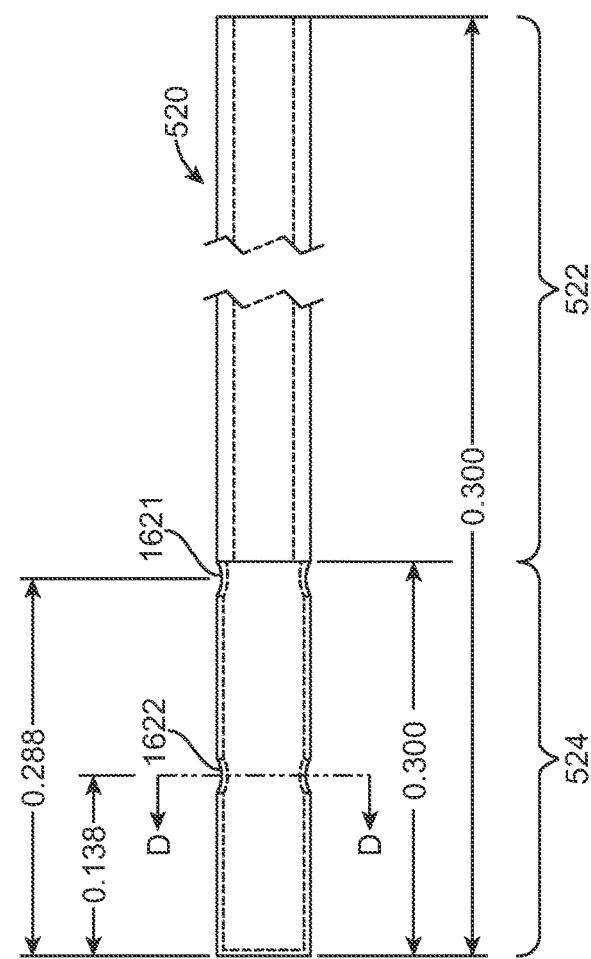

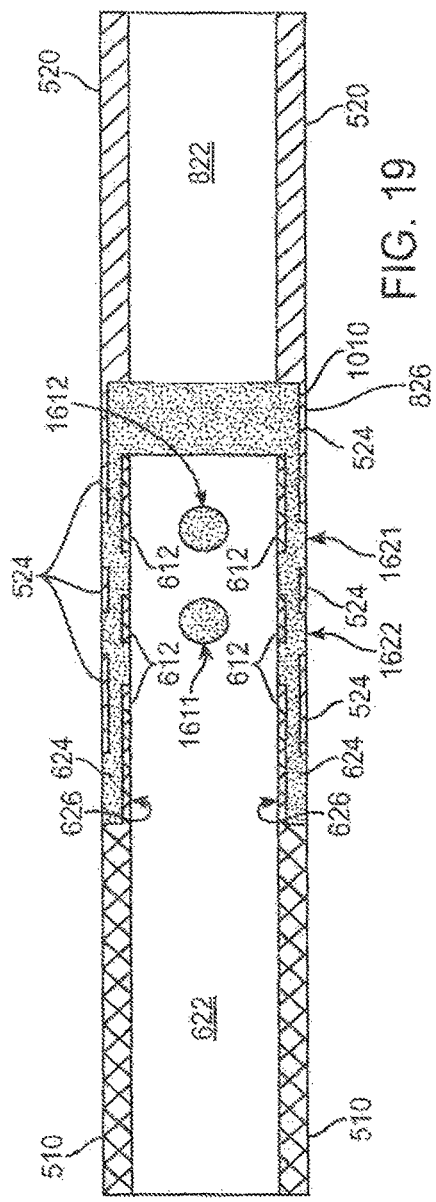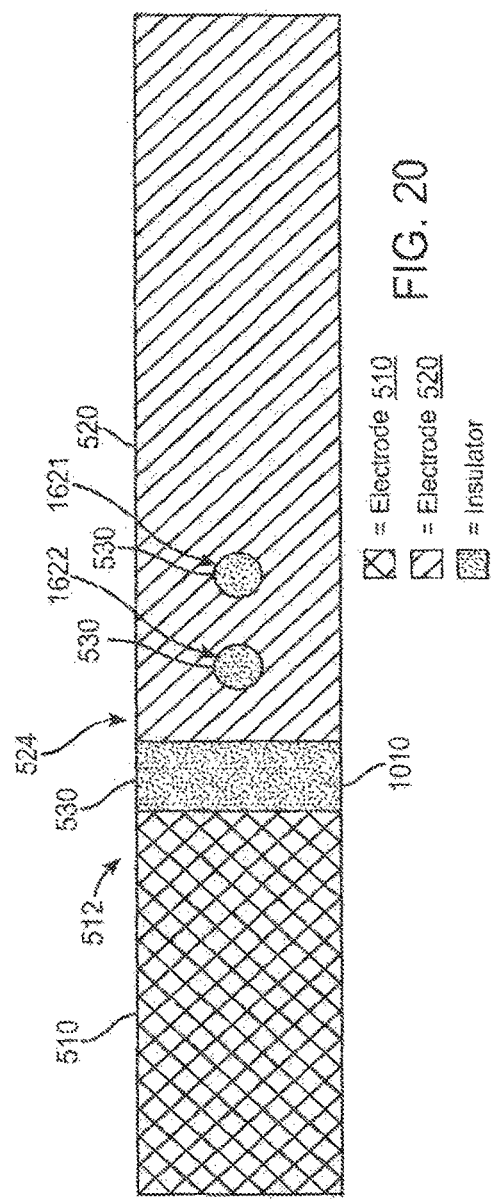

B-B

A-A

D-D

C-C

F-F

E-E

BIPOLAR ELECTROSURGICAL PROBE HAVING INSULATED OVERLAPPING CONDUCTIVE ELEMENTS

RELATED APPLICATION DATA

This application is a continuation of U.S. patent application Ser. No. 12/262,073, filed on Oct. 30, 2008, which claims priority to U.S. Provisional Patent Application No. 60/985,201, filed on Nov. 3, 2007. The foregoing applications are incorporated by reference as if set forth fully herein.

FIELD OF INVENTION

The present invention relates to electrosurgical devices.

BACKGROUND

Electrosurgery is a widely used surgical procedure for treating tissue abnormalities. For example, it is known to use radio frequency (RF) energy to treat or ablate cancerous lesions in the liver, kidney, lungs and other soft tissues. RF ablation occurs as a result of a high frequency alternating current (AC) flowing from the tip of an electrode through the surrounding tissue. Ionic agitation is produced in the tissue around the electrode tip as the ions attempt to follow the change in direction of the alternating current. This ionic agitation creates frictional heating and necrosis of the tissue around the electrode. Such procedures may be performed through an open abdominal incision or via laparoscopy performed through multiple, small skin incisions, and can also be conducted percutaneously through small skin incisions.

Electrosurgical devices that can be used for tissue ablation using RF energy generally fall into one of two categories, monopolar devices and bipolar devices. Monopolar electrosurgical devices typically include an electrosurgical probe having a first or "active" electrode extending from one end. The electrosurgical probe is electrically coupled to an electrosurgical generator, which provides a high frequency electrical current. During an operation, a second or "return" electrode, having a much larger surface area than the active electrode, is positioned in contact with the skin of the patient. The surgeon may then bring the active electrode in close proximity to the tissue and activate a switch, which causes electrical current to arc from the distal portion of the active electrode and flow through tissue to the larger return electrode. Bipolar electrosurgical devices do not use a return electrode. Instead, a second electrode is closely positioned adjacent to the first electrode, with both electrodes being attached to an electrosurgical probe. As with monopolar devices, the electrosurgical probe is electrically coupled to an electrosurgical generator. When the generator is activated, electrical current arcs from the end of the first electrode to the end of the second electrode and flows through the intervening tissue. The gauge or size of electrodes of RF ablation probes is often minimized in order to reduce trauma to the surgical site and facilitate accurate placement of the probe so that target tissue can be ablated with minimal damage to surrounding healthy tissue.

One known bipolar electrosurgical probe configuration is shown in FIGS. 1-3. A typical bipolar electrosurgical probe 10 includes electrode or needle members 12 and 14 and an insulation member 16 between ends of the electrodes 12 and 14 to provide bipolar modality. In known devices, the insulation member 16 is a non-conductive glue or adhesive. A distal end 13 of one electrode 12 and a proximal end 15 of another electrode 14 are attached to the insulation member there between. Glue may flow over the edges of the electrodes 12 and 14 and be smoothed or flush with the electrodes if the electrodes are machined with a lathe.

While such electrosurgical probes have been used effectively in the past, they can be improved. In particular, the strength and durability of bipolar electrosurgical probes can be enhanced to withstand forces and loads that are encountered during placement and removal of the probes. For example, the insulation glue or plastic member 16 positioned between ends of two conductive electrodes 12 and 14 is flexible relative to the electrodes 12 and 14, which are typically stainless steel. The flexible glue or plastic insulation member 16, therefore, is a weak point in the probe.

For example, referring to FIG. 4, during use, the tip 18 of the probe 10 may encounter bone or another hard material 20. The stainless steel electrodes 12 and 14 can withstand these forces, but the probe 10 may buckle or kink 30 at the weak point of the probe 10, i.e., at the glue or plastic insulation member 16. These types of failures may be more common when using probes having small diameter or thin walled electrodes 12 and 14, which are used to reduce trauma to surrounding tissue. Thus, while smaller and thinner electrodes reduce tissue trauma, they also have weaker insulation members 16 and are more likely to buckle or kink. Thus, the desire for small electrode dimensions to reduce tissue trauma must be balanced against a probe having sufficient strength to withstand compression, tension and torque or rotational forces or loads encountered during ablation procedures.

Accordingly, it would be desirable to have electrosurgical probes with improved strength and structural integrity. Further, it would be desirable to have such improved strength and integrity while maintaining small electrode dimensions to reduce trauma to surrounding healthy tissue.

SUMMARY

According to one embodiment, a bipolar electrosurgical probe includes first and second tubular electrodes carried by a probe shaft and an insulation member. At least a portion of the insulation member is disposed between overlapping ends of the first and second tubular electrodes.

According to another embodiment, a bipolar electrosurgical probe includes first and second tubular electrodes carried by a probe shaft and an insulation member disposed in a lumen defined by a proximal end of the second electrode. At least a portion of the insulation member is disposed between an outer surface of the distal end of the first electrode and an inner surface of the proximal end of the second electrode.

According to another embodiment, a bipolar electrosurgical probe includes first and second tubular electrodes carried by a probe shaft and an insulation member disposed between an outer surface of a distal end of the first electrode and an inner surface of a proximal end of the second electrode. A thickness of a wall of the distal end of the first electrode differs from a thickness of the wall of a proximal end of the first electrode, and a thickness of a wall of the proximal end of the second electrode differs from a thickness of the wall of a distal end of the second electrode.

According to a further embodiment, a bipolar electrosurgical probe includes first and second tubular electrodes carried by a probe shaft and an insulation member. At least a portion of the insulation member is disposed between concentric overlapping ends of the first and second tubular electrodes. The overlapping ends can be a distal cylindrical wall of the first electrode and a proximal cylindrical wall of the second electrode.

In another embodiment, a bipolar electrosurgical probe includes first and second cylindrical electrodes carried by a probe shaft. A portion of the insulation member is disposed between an outer surface of a distal end of the first electrode and an inner surface of a proximal end of the second electrode, and a second portion of the insulation member forms part of an outer surface of the electrode.

According to an alternative embodiment, a bipolar electrosurgical probe includes first and second electrodes carried by a probe shaft. The first electrode defines at least one aperture extending through a wall thereof and a second electrode defines at least one aperture extending through a wall thereof. An insulation member is disposed between an outer surface of a distal end of the first electrode and an inner surface of a proximal end of the second electrode. Additionally, portions of the insulation member are disposed in the apertures through the walls of the first and second electrodes.

According to a further alternative embodiment, a bipolar electrosurgical probe includes first and second electrodes carried by a probe shaft and an insulation member disposed between the first and second electrodes. At least one electrode defines an aperture extending through a wall of the at least one electrode. A portion of the insulation member extends into the aperture.

Another alternative embodiment is directed to a bipolar electrosurgical probe that includes first and second electrodes carried by a probe shaft and an insulation member disposed between the first and second electrodes. Each electrode defines an aperture extending through the electrode, and a portion of the insulation member extends into each aperture.

Another embodiment is a method of forming a bipolar electrosurgical probe. The method includes inserting a distal end of a first electrode into a lumen defined by a wall of a proximal end of a second electrode, and disposing an insulation member between an outer surface of a distal end of the first electrode and an inner surface of a proximal end of the second electrode.

In one or more embodiments, the electrodes can be concentric. Further, in one or more embodiments, a thickness of a wall of the distal end of the first electrode is less than a thickness of the wall of a proximal end of the first electrode, e.g., the thickness of the wall of the distal end of the first electrode can be about 0.003" to about 0.006", and the thickness of the wall of the proximal end of the first electrode can be about 0.013". Further, a thickness of the wall of a proximal end of the second electrode is less than a thickness of the wall of a distal end of the second electrode. For example, the thickness of the wall of the proximal end of the second electrode can be about 0.003" to about 0.006", and the thickness of the distal end wall of the second electrode can be about 0.013".

In one or more embodiments, a distal end of the first electrode is disposed inside a lumen defined by a wall of the proximal end of the second electrode. In one or more embodiments, a width of a lumen defined by a wall of the distal end of the first electrode can less than a width of a lumen defined by a wall of a proximal end of the first electrode. Further, a width of a lumen defined by a wall of the proximal end of the second electrode can be greater than a width of a lumen defined by a wall of a distal end of the second electrode. For example, the width of the lumen defined by the proximal end wall of the second electrode can be about 0.051" to about 0.057", and the width of the lumen defined by the distal end wall of the second electrode can be about 0.045".

In one or more embodiments, the insulation member is a resin and can be disposed between surfaces of different electrodes using an adhesive or an injection process. The insulation member can assume a shape of a space between a surface of the distal end of the first electrode and a surface of the proximal end of the second electrode. In one or more embodiments, the insulation member extends through apertures defined through a wall of an electrode. A non-conductive sleeve can be disposed between an inner surface of the distal end of the first electrode and an outer surface of the proximal end of the second electrode in order to maintain concentric electrodes.

Other aspects of embodiments are described herein and will become apparent upon reading the following detailed description with reference to the accompanying drawings.

BRIEF DESCRIPTION OF THE DRAWINGS

Referring now to the drawings in which like reference numbers represent corresponding parts throughout and in which:

FIG. 13 is a cross-sectional front view along line A-A in FIG. 11;

FIG. 14 is a cross-sectional front view along line B-B in FIG. 11;

FIG. 15 is a cross-sectional front view along line C-C in FIG. 11;

FIG. 17A is a perspective view of an electrode having an end having an enlarged inner diameter and an aperture formed through a wall of an electrode according to one embodiment;

FIG. 17B is a partial cross-sectional view of an electrode having an end having an enlarged inner diameter and an aperture formed through a wall of an electrode according to one embodiment;

FIG. 18A is a perspective view of an electrosurgical probe in which an end of the electrode shown in FIGS. 16A-B is inserted into a lumen of an end of the electrode shown in FIGS. 17A-B;

FIG. 18B is a partial cross-sectional side view of an electrosurgical probe in which an end of the electrode shown in FIGS. 16A-B is inserted into a lumen of an end of the electrode shown in FIGS. 17A-B;

FIG. 19 is a partial cross-sectional view further illustrating an electrosurgical probe configured as shown in FIGS. 16A-18B;

FIG. 20 is a side view further illustrating the electrosurgical probe shown in FIG. 19;

DETAILED DESCRIPTION OF ILLUSTRATED EMBODIMENTS

The illustrated embodiments are directed to electrosurgical probes with improved strength and durability while maintaining small electrode dimensions to apply RF energy at target areas while reducing or minimizing damage to surrounding healthy tissue, thereby allowing for easier and more flexible positioning and withdrawal of the probes during ablation procedures.

Figure 1:
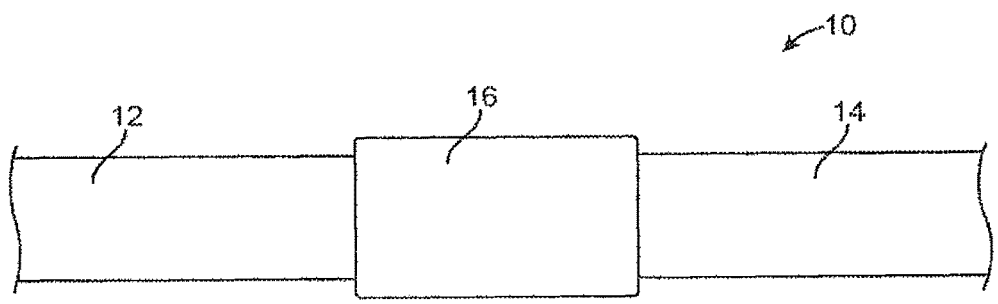
FIG. 1 is a partial side view of a known bipolar electrosurgical probe having an insulation member between ends of conductive electrodes.
Figure 2:
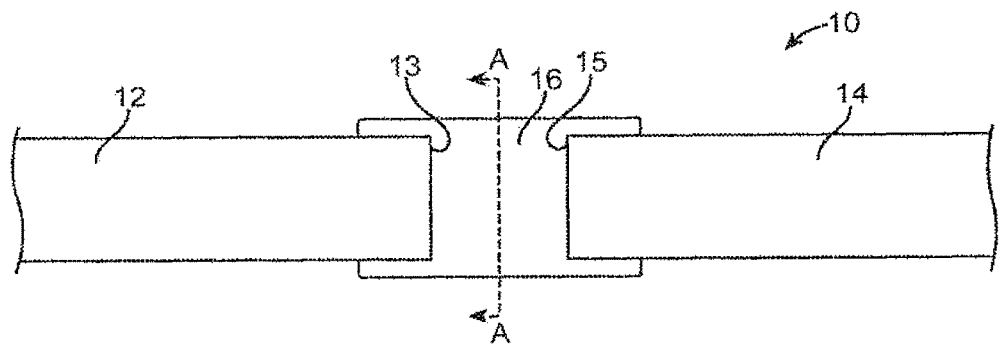
FIG. 2 is a cross-sectional side view of FIG. 1 along a length of the electrosurgical probe.
Figure 3:
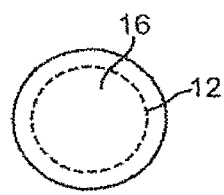
FIG. 3 is a cross-sectional front view of the electrosurgical probe shown in FIG. 1 along line A-A in FIG. 2 showing a middle section having only insulation material.
Figure 4:
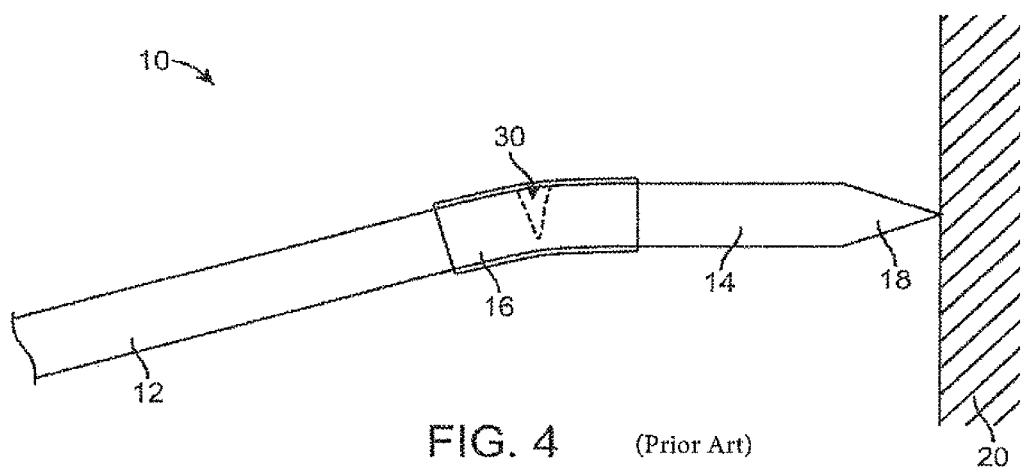
FIG. 4 generally illustrates how known bipolar electrosurgical probes bend or kink at an insulation member by application of force.
Figure 5:
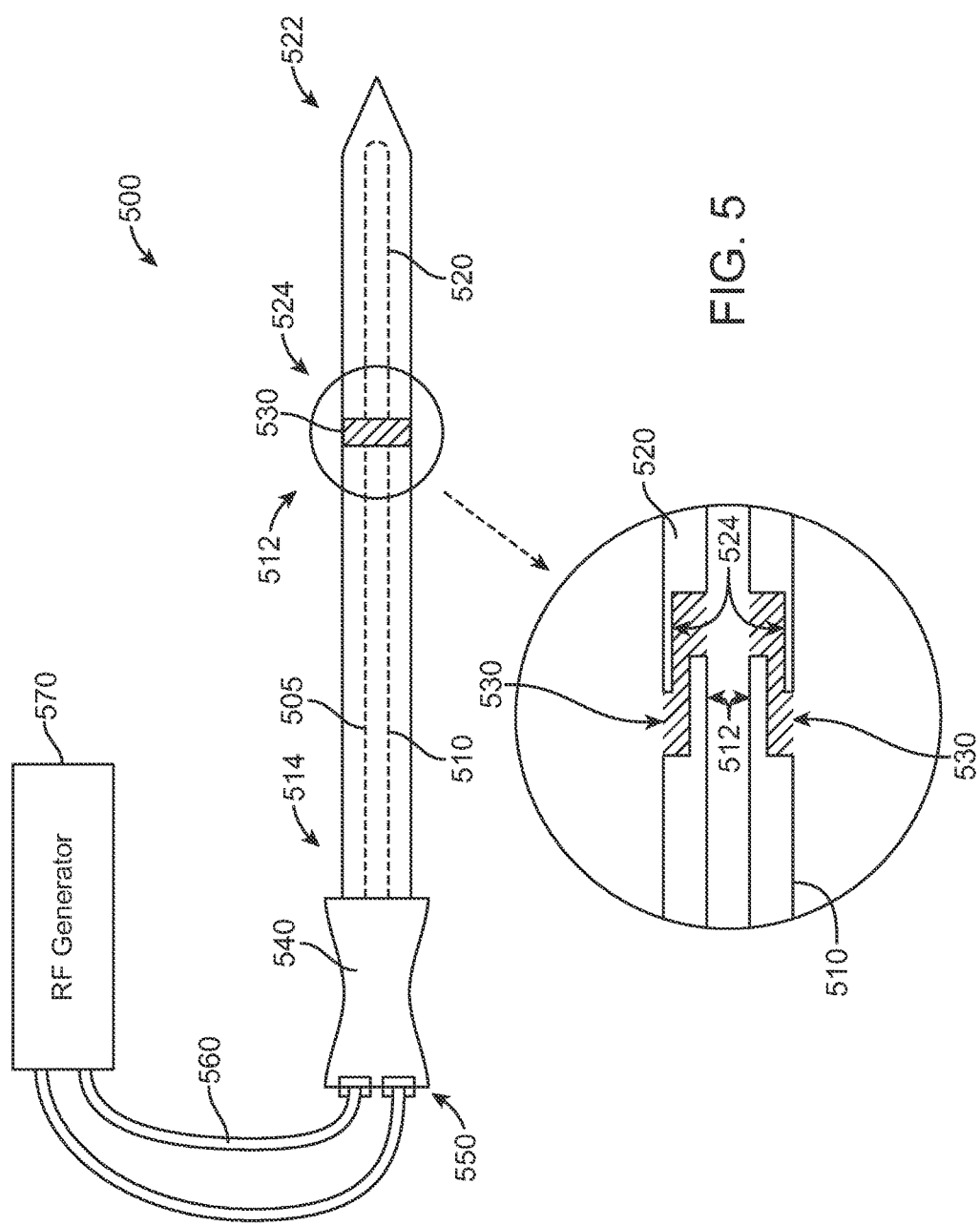
FIG. 5 is a partial cross-sectional side view of an electrosurgical probe having overlapping electrode ends that extend into or are connected to the insulation member according to one embodiment.

Referring to FIG. 5, according to one embodiment, an electrosurgical probe or probe assembly 500 (generally "probe" 500) includes a probe member or shaft 505 (shown generally as a phantom line) that carries a first electrically conductive electrode 510, a second electrically conductive electrode 520, and an insulation or non-conductive member 530. The insulation member 530 separates the electrodes 510 and 520. A handle 540 receives an end or shaft 505 of the probe 500 and includes one or more connectors or interfaces 550 that connect the probe to a RF generator 570 or other suitable current source via electrical leads 560. The RF generator 570 conveys electrical current to the probe 500. The RF generator 570 can be a conventional RF power supply that operates at a frequency in the range from 200 KHz to 1.25 MHz, with a conventional sinusoidal or non-sinusoidal wave form. Suitable RF generators 570 are available from commercial vendors, such as Boston Scientific Corporation of San Jose, Calif., which markets these power supplies under the trademarks RF2000® (100 W) and RF3000® (200 W).

In the illustrated embodiment, an end 512 of an electrode 510 extends or protrudes into the insulation member 530, which separates ends 512 and 524 of respective ends 510 and 520 for bipolar operation. In the illustrated embodiment, the ends 512 and 524 overlap and provide support to the insulation member 530 to advantageously eliminate or reduce bending or kinking of the probe 500 at the insulation member 530 while maintaining desired small probe 500 diameters for reducing trauma to surrounding tissue.

FIG. 5 illustrates electrodes 510 and 520 and respective ends 512 and 522 of thereof having a cylindrical or tubular shape. Persons skilled in the art will appreciate, however, that embodiments can involve electrodes 510 and 520 that are other, non-cylindrical shapes. Further, FIG. 5 illustrates concentric cylindrical or tubular electrodes 510 and 520. However, in other embodiments, the electrodes 510 and 520 are not necessarily concentric. Accordingly, FIG. 5 is provided as an example of how embodiments can be implemented, and for purposes of illustration and explanation, this specification illustrates concentric cylindrical or tubular electrodes 510 and 520.

Figure 6:
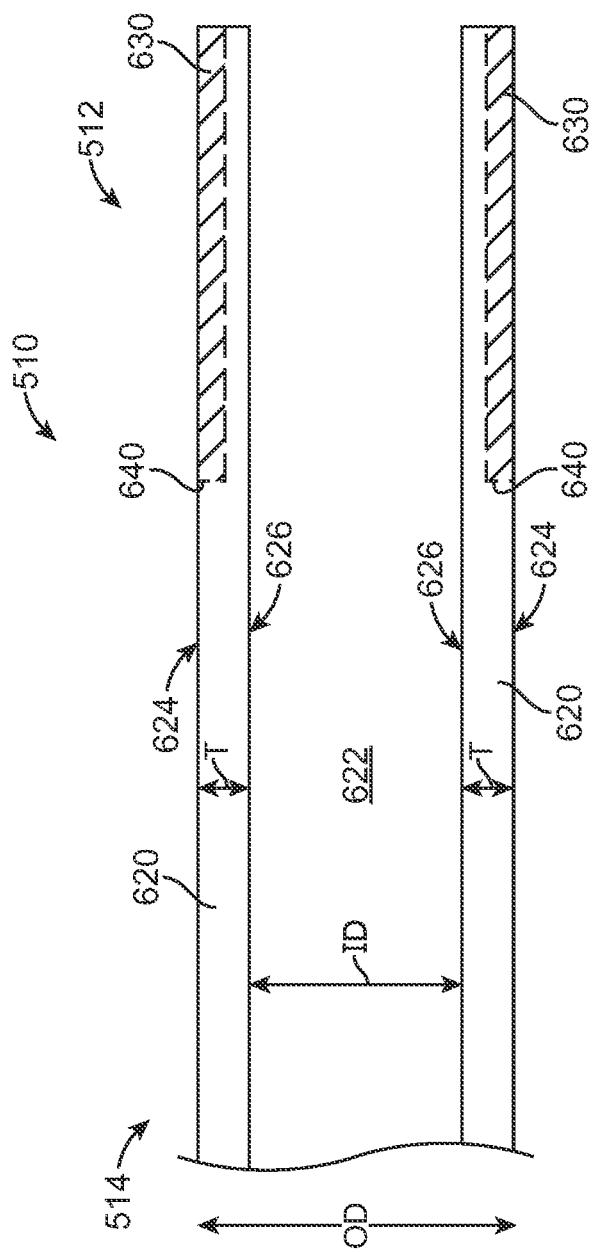
FIG. 6 is partial cross-sectional side view of a first electrode for use with various embodiments.
Figure 7:
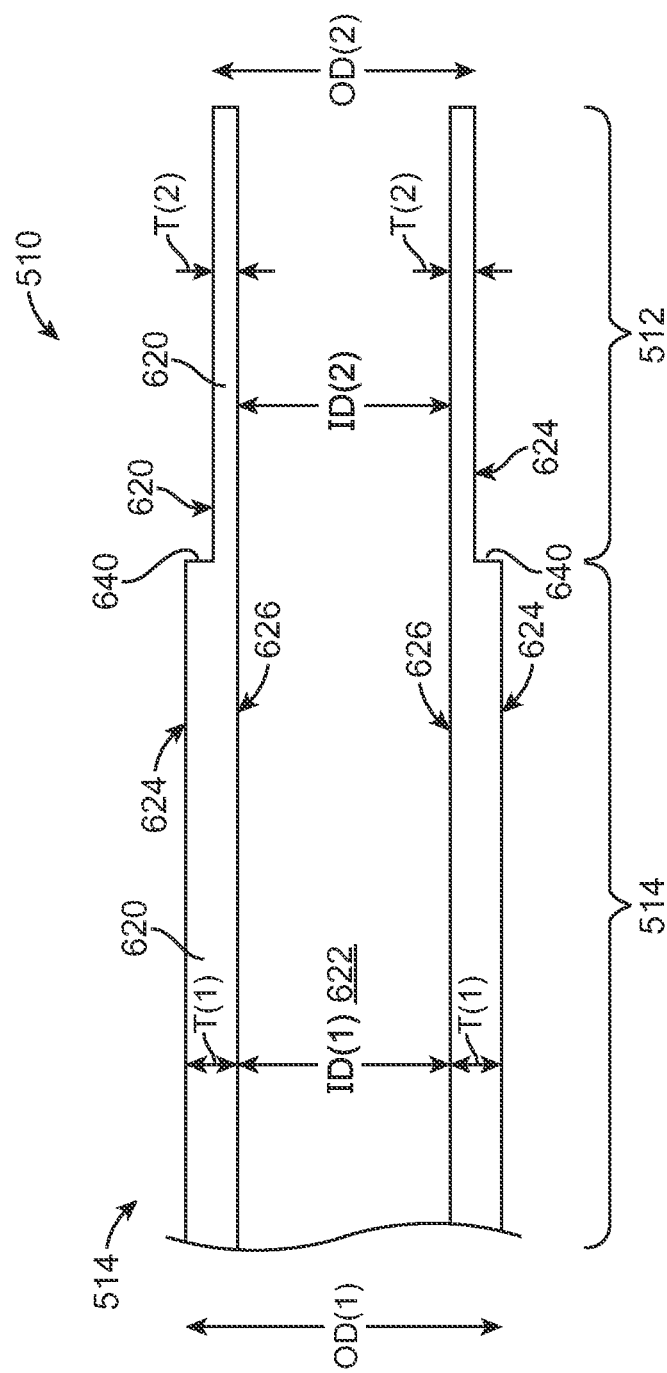
FIG. 7 is a partial cross-sectional side view of the first electrode shown in FIG. 6 in which an outer surface of a wall of the first electrode has been removed to form a distal end having a reduced outer diameter end according to one embodiment.
Figure 8:
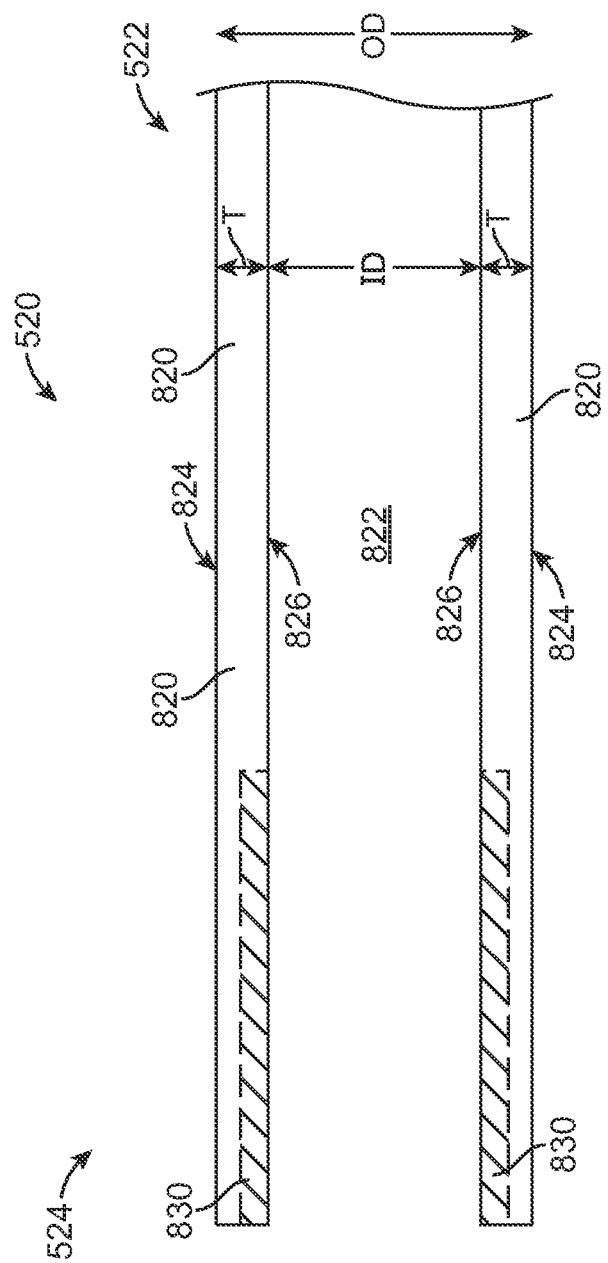
FIG. 8 is a partial cross-sectional side view of a second electrode for use with various embodiments.
Figure 9:
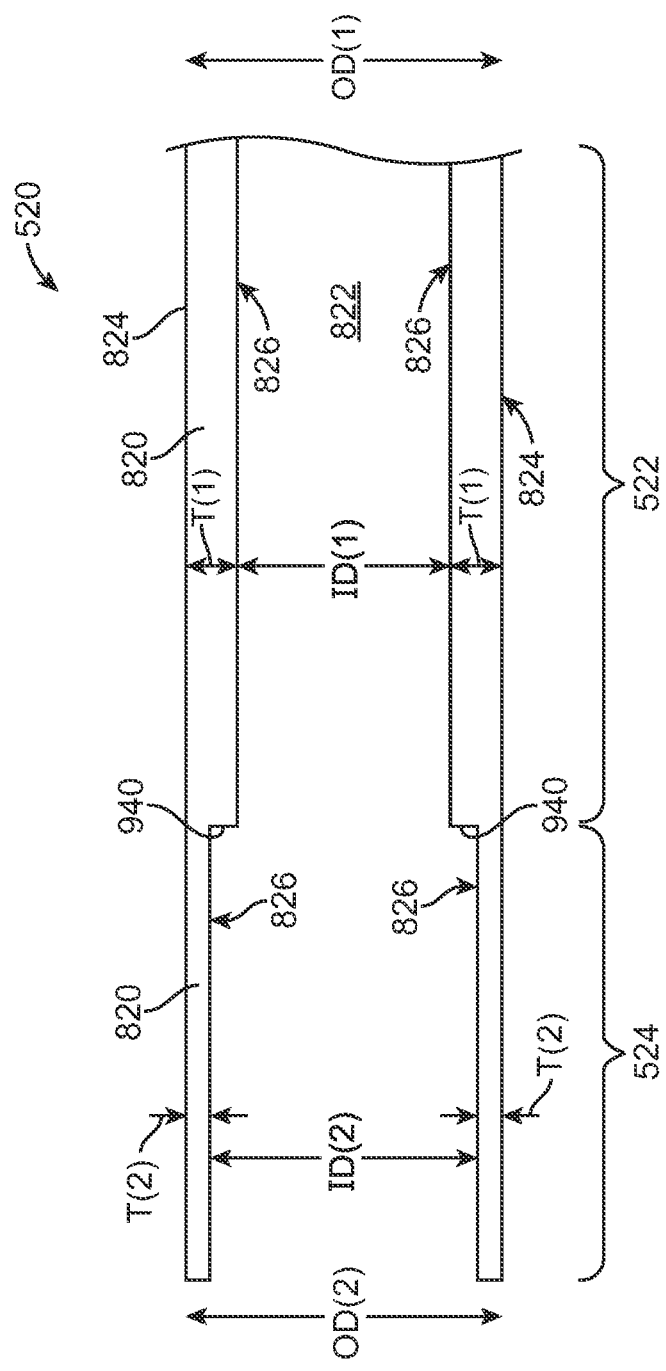
FIG. 9 is a partial cross-sectional side view of the second electrode shown in FIG. 8 in which an inner surface of a wall of the second electrode has been removed or bored to a proximal end having an enlarged inner diameter according to one embodiment.
Figure 10:
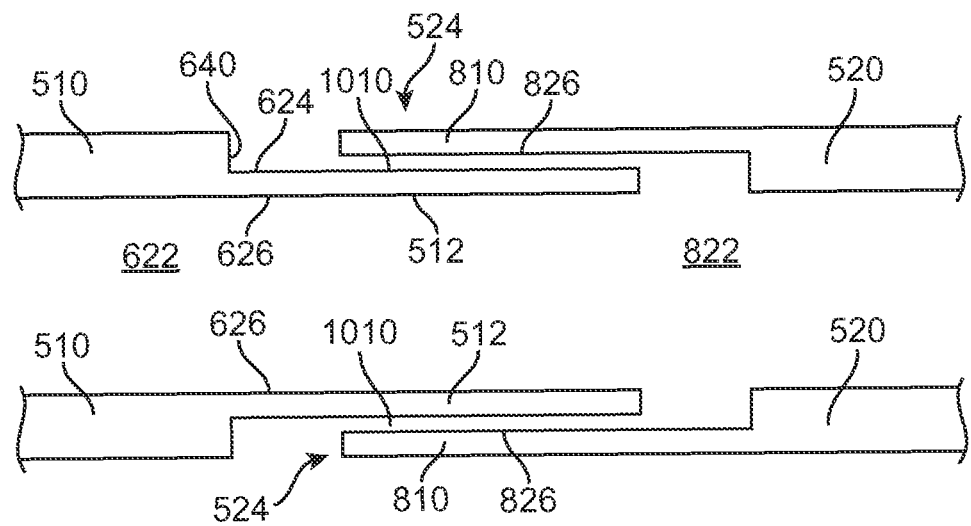
FIG. 10 is a partial cross-sectional side view of a distal end having a reduced outer diameter inserted into a proximal end having an enlarged inner diameter according to one embodiment.
Figure 11:
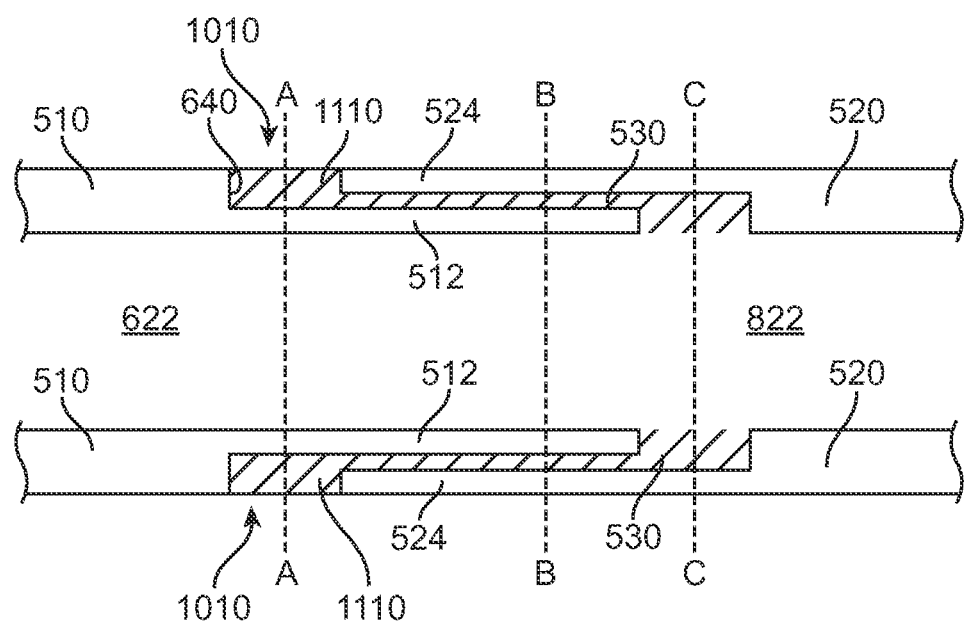
FIG. 11 is a partial cross-sectional side view illustrating an insulation material disposed in a space between overlapping surfaces of ends of first and second electrodes according to one embodiment.

FIGS. 6 and 7 illustrate a first electrode 510 and FIGS. 8 and 9 illustrate a second electrode 520 that can be used with various embodiments. FIGS. 10 and 11 illustrate how the electrodes 510 and 520 are configured for an overlapping and insulated arrangement.

Referring to FIG. 6, the first electrode 510 includes a left or proximal end 514, a right or distal end 512 and an elongated cylindrical or tubular body or wall 620 defining a lumen 622 extending along a length of the wall 620. The wall 624 has an outer surface 624 and an inner surface 626. The first electrode 510 can, for example, have a length of about 1-12", an outer diameter (OD) of about 0.071", an outer wall 620 having a thickness (T) of about 0.013", and a lumen having an inner diameter (ID) of about 0.045".

Referring further to FIG. 7, the distal end 512 of the first electrode 510 can be modified by removing a section 630 of the wall 620, e.g. by machining or other known suitable methods. In the illustrated embodiment, the section 630 that is removed is a part of an outer surface 624 of the wall 620. FIG. 7 illustrates the first electrode 510 following removal of the section 630, thereby forming a reduced diameter distal end 512 and an edge 640 at the step-down transition from the original wall 620 thickness T(1) to the reduced wall 620 thickness T(2).

The original wall 620 thickness T(1) can be about 0.013", and the reduced wall 620 thickness T(2) can be about 0.003" to about 0.006," e.g., about 0.0035". The outer diameter of the wall 620 can be reduced from an OD(1) of about 0.071" to a smaller OD(2) of about 0.051" to about 0.057," e.g., about 0.052" depending on how large of a section 630 is removed. Thus, the outer diameter OD(2) is less than the original outer diameter OD(1), and the inner diameter ID(2) is the same as the inner diameter ID(1) since the section 630 was removed from the outer surface 624 of the wall 620.

Referring to FIG. 8, one suitable second electrode 520 includes a left or proximal portion or end 524, a right or distal portion or end 522 and an elongated cylindrical or tubular body or wall 820 defining a lumen 822 extending along a length of the wall 820. The second electrode 520 has an outer surface 824 and an inner surface 826. The dimension of the second electrode 520 can be the same as or similar to the dimensions of the first electrode 510.

Referring further to FIG. 9, a proximal end 524 of the second electrode 520 can be modified by removing a section 830 of the wall 820. In the illustrated embodiment, the section 830 that is removed is a part of an inner surface 826 of the wall 820. FIG. 9 illustrates the second electrode 520 following removal of the section 830, thereby forming an edge 940 at the point of the transition from the original wall thickness T(1) to a thickness T(2) that is less than the wall thickness T(1). The outer diameter OD(2) is the same as the outer diameter OD(1), and the inner diameter ID(2) is larger than the original inner diameter ID(1) since the section 830 was removed from an inner surface 826 of the wall 820.

For purposes of illustration and explanation, the boundary between the proximal end or portion 514 of the first electrode and the distal end or portion 512 of the first electrode is the edge 640 or the point of transition. Similarly, for purposes of illustration and explanation, the boundary between the proximal end or portion 524 of the second electrode 520 and the distal end or portion 522 of the second electrode is the edge 940 or the point of transition. Persons skilled in the art, however, will appreciate that the length of the wall 620 section having the reduced thickness can vary, and the distal and proximal portions 512 and 524 can have various lengths.

Further, persons skilled in the art will also appreciate that the labels "first," "second," "proximal," and "distal" are used in this specification to identify different elements or sections of an electrode rather than implying any particular sequence or configuration. Thus, although the figures illustrate the first electrode 510 having a distal end 512 with a reduced outer diameter and the second electrode 520 having a bored proximal end 524, embodiments can also be implemented by a first electrode 510 having a bored distal end 512 and the second electrode 520 having a proximal end 524 with a reduced outer diameter. Embodiments, therefore, can be implemented in various manners, and the particular labels that are used in a general manner are used to identify different electrodes and sections thereof.

Additionally, rather than forming or modifying electrodes 510 and 520 by machining or another suitable as described above, embodiments can be implemented using electrodes 510 and 520 that are manufactured or pre-formed with ends having desired dimensions so that it is not necessary to remove sections 640 and 830 from respective electrodes 510 and 520. Accordingly, embodiments can be applied to standard electrodes 510 and 520 that are modified by surface removal and, in addition, electrodes 510 and 520 that are manufactured in this manner.

Referring to FIG. 10, the first and second electrodes 510 and 520 are shaped so that the reduced outer diameter distal end 512 of the first electrode 510 can be inserted into the lumen 822 defined by the proximal bored end 524 of the second electrode 520. As generally illustrated in FIG. 10, the thicknesses of the wall 620 at the distal end 512 of the first electrode 510 and at the proximal end 524 of the second electrode 520 are such that when the distal end 512 of the first electrode 510 is inserted into the lumen 822, a space, gap or aperture 1010 exists between the outer surface 624 of the distal end 512 of the first electrode 510 and an inner surface 826 of the proximal end 524 of the second electrode 520.

Referring to further FIG. 11, an insulation member 530 or insulation material 1110 that forms an insulation member can be disposed in the space 1010 between overlapping electrodes 510 and 520. In one embodiment, the insulation material 1110 can be injected into the space 1010. For example, an insulation material 1110, such as an insulating plastic or resin, can be injected into a circumferential space 1010 between an edge 640 of the first electrode 510 and proximal end 524 of the second electrode 520. The material 1110 sets or dries to form the insulation member 530, which separates the first and second electrodes 510 and 520 and prevents a short between the electrodes 510 and 520 to maintain bipolar modality. One suitable insulation material 1110 that can be utilized is Ultem® available from General Electric Company (General Electric Plastics), Schenectady, N.Y. Suitable machines for performing injection or micromolding of resin material 1110 are available from ARBURG GmbH & Co. KG, Arthur-Hehl-Strasse, 72290 Lossburg, Germany. Embodiments can be implemented with other materials 1110 and other suitable micro-molding equipment.

In other embodiments, rather than injection or micro-molding, the insulation member 530 can be disposed or placed in the space 1010 by using a suitable adhesive. In one embodiment, plastic components or sleeves can be secured in place with an adhesive to separate the electrodes 510 and 530. For example, an inner surface of an insulative plastic component can be secured or adhered around a distal end 512 of the first electrode, and an outer surface of the insulative plastic component can be secured or adhered to an inner surface of the second electrode 520.

Thus, persons skilled in the art will appreciate that both injection molding and materials and other materials and techniques can be used to provide an insulation member 530 between overlapping ends 512 and 524 of the electrodes 510 and 520. Thus, when this specification refers to injection molding and example resin materials and methods for separating electrodes, persons skilled in the art will appreciate that other methods and systems can also be utilized. Similarly, when this specification refers to plastic/adhesive techniques, persons skilled in the art will appreciate that injection molding and other techniques and systems can also be utilized.

Figure 12:
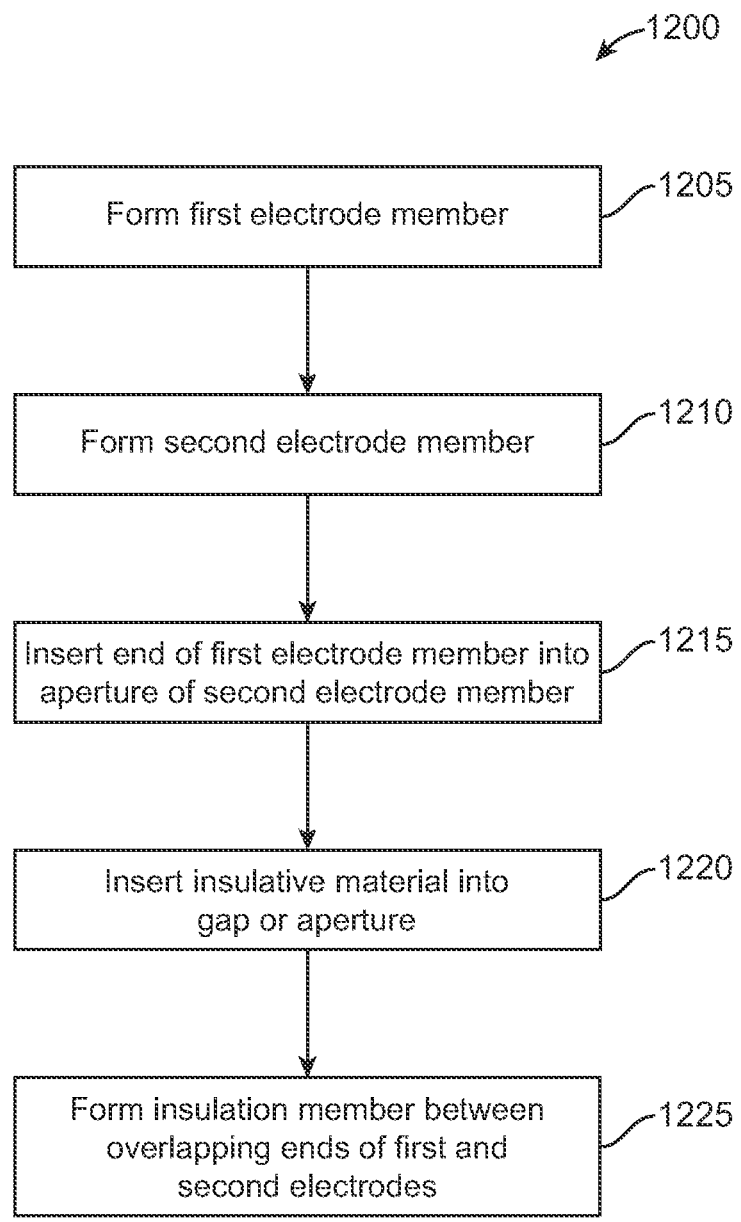
FIG. 12 is a flow chart of a method of manufacturing a bipolar electrode probe according to one embodiment.
Figure 16A:
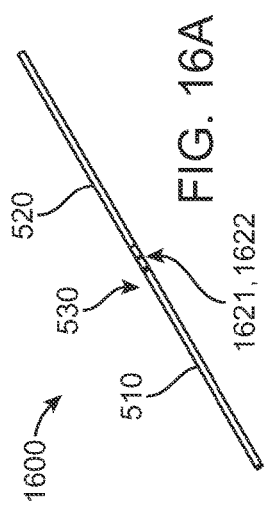
FIG. 16A is a perspective view of an electrode having an end having a reduced outer diameter and an aperture formed through a wall of an electrode according to one embodiment.
Figure 16B:
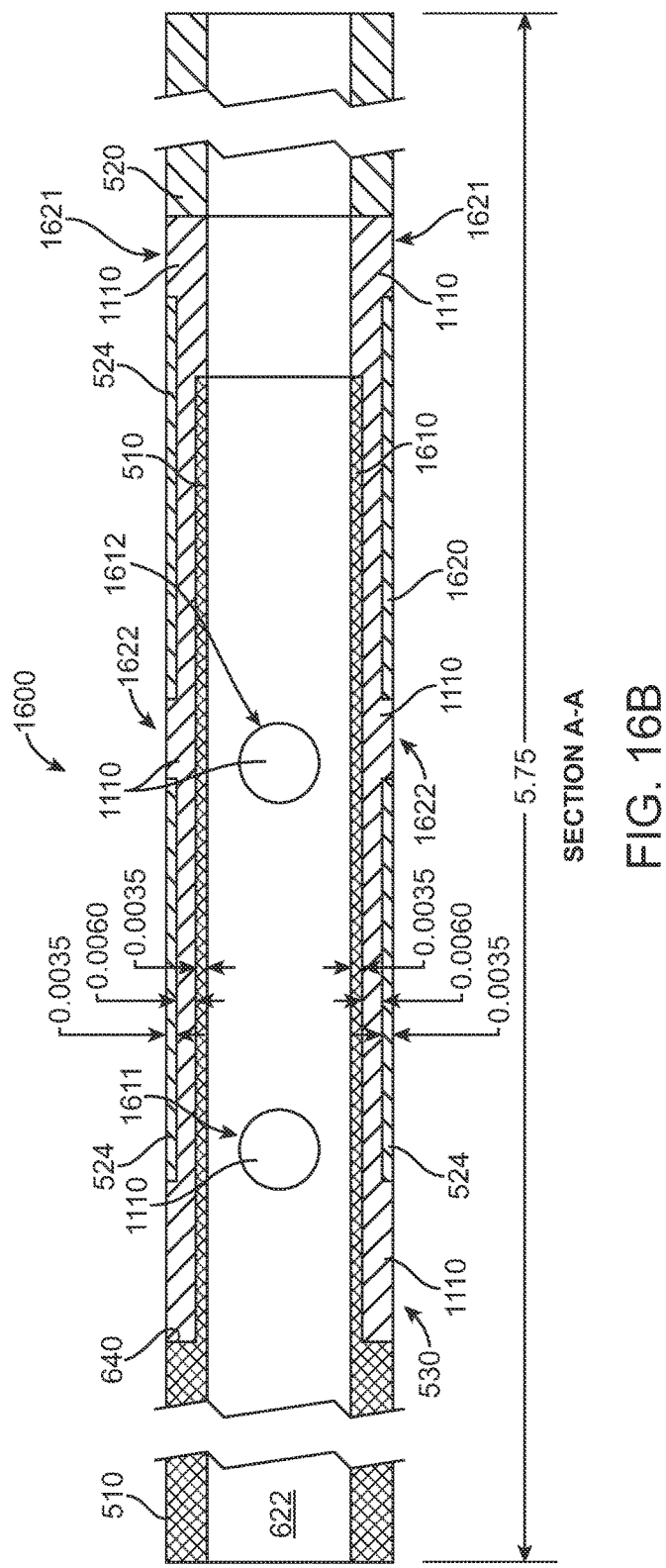
FIG. 16B is a partial cross-sectional view of an electrode having an end having a reduced outer diameter and an aperture formed through a wall of an electrode according to one embodiment.

Thus, referring to FIG. 12, according to one embodiment, a method 1200 of making a bipolar electrosurgical probe includes, if necessary, forming or making a first electrode in step 1205 (e.g., as shown in FIG. 7) and, if necessary, forming or making a second electrode in step 1210 (e.g., as shown in FIG. 9). Steps 1205 and 1210 may involve reducing or increasing a diameter of an end of one or more electrodes. Steps 1210 and 1215 may not be necessary if the first and second electrodes are already provided or made with the desired diameters and configurations. In step 1215, an end of one electrode is inserted into a lumen of another electrode. Referring again to FIG. 11, for example, a reduced outer diameter distal end of the first electrode can be inserted into the lumen of proximal end having an enlarged inner diameter. In step 1220, an insulation member or material is inserted, e.g. injected into, the space between the distal end of the first electrode and the proximal end of the second electrode so that the insulation member is disposed between overlapping ends of the electrodes. According to one embodiment, the insulation member is composed of a plastic or resin and can be formed by injection or micro-molding. In step 1225, if plastic or resin is used, the injected material dries, forms or sets to form an insulation member between overlapping distal and proximal ends of respective first and second electrodes.

With this configuration and the method of making a bipolar electrosurgical probe, as shown in FIGS. 13-15, the insulation member 530 is advantageously provided with one or more supports in the form of a distal end 512 of the first electrode 510 and/or a proximal end 524 of the second electrode 520. In the illustrated embodiment, the ends 512 and 524 of the electrodes 510 and 520 are tubular bodies, and the insulation member 530 is in the form of concentric rings.

FIG. 13 is a cross-sectional view of FIG. 11 along line A-A in which the insulation member 530 or insulation material 1110 or member 530 (generally referred to as an insulation member 530) extends around the outer surface 624 of the distal end 512 of the first electrode 510. Thus, this portion of the insulation member 530 forms an outer surface of the probe 500 and is visible to a user. FIG. 14 is a cross-sectional view of FIG. 11 along line B-B in which the insulation member 530 is sandwiched between or bounded by overlapping ends 512 and 524 of respective first and second electrodes 510 and 520. In the illustrated embodiment, the insulation member 530 is sandwiched between an outer surface 626 of the distal end 512 of the first electrode 510 and an inner surface 826 of the proximal end 524 of the second electrode 510. FIG. 15 is a cross-sectional view of FIG. 11 along line C-C in which the insulation member 530 extends along an inner surface 826 of the proximal end 524 of the second electrode 520.

FIGS. 16A-18B illustrate another embodiment of a probe 1600 that includes first and second electrodes 510 and 520 separated by an insulation member 530 (as discussed above) and one or more apertures that are formed through the walls of one or more electrodes. In the illustrated embodiment, a first electrode 510 includes apertures 1611 and 1612, and a second electrode 520 includes aperture 1621 and 1622. Portions of the insulation member 530 extend through the apertures and advantageously absorb tensile and torsion forces. Further, the portions of the insulation member 530 extending into the apertures prevent the two electrodes 510 and 520 from pulling apart from each other. Additionally, the one or more or all of the apertures can also be used to inject insulation material 1110 into the space 1010 between the outer surface 624 of the distal end 512 of the first electrode 510 and an inner surface 826 of the proximal end 524 of the second electrode 520. Thus, a material 1110, such as an insulating plastic or resin, can be injected into a circumferential space 1010 between an edge 640 of the first electrode 510 and a proximal end 524 of the second electrode 520 and/or injected into one or apertures formed through a wall of an electrode so that the injected material 1110 fills the space 1010 between the outer surface 624 of the distal end 512 of the first electrode 510 and the inner surface 626 of the proximal end 524 of the second electrode 520 and sets to form the insulation member 530.

Figure 21:
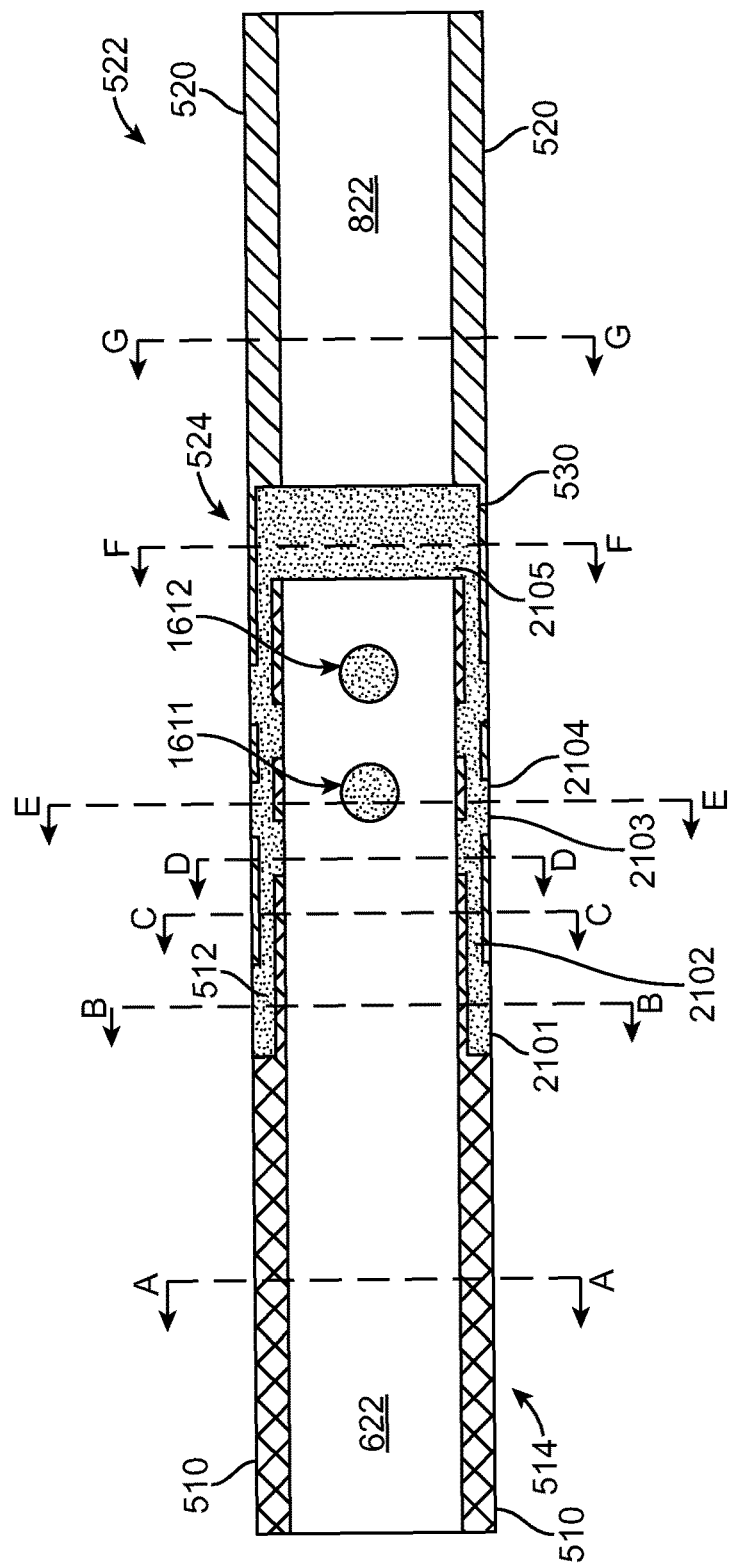
FIG. 21 is the partial cross-sectional view shown in FIG. 19 including cross-sectional dividing lines A-A to G-G.
Figure 23:
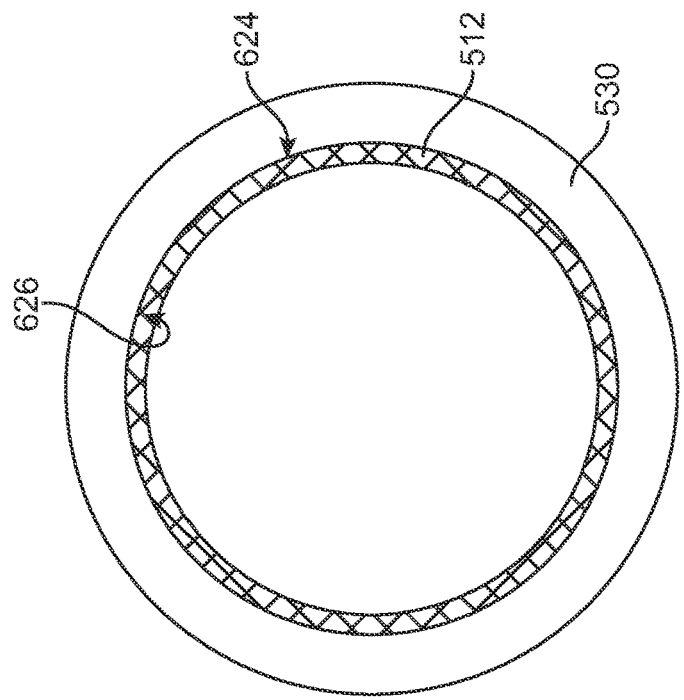
FIG. 23 is a cross-sectional view of FIG. 21 along line B-B.
Figure 22:
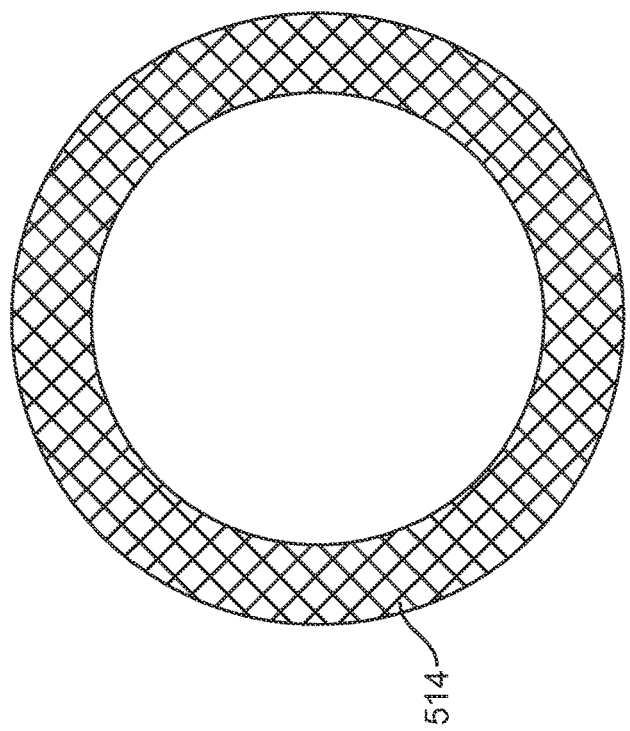
FIG. 22 is a cross-sectional view of FIG. 21 along line A-A.
Figure 24:
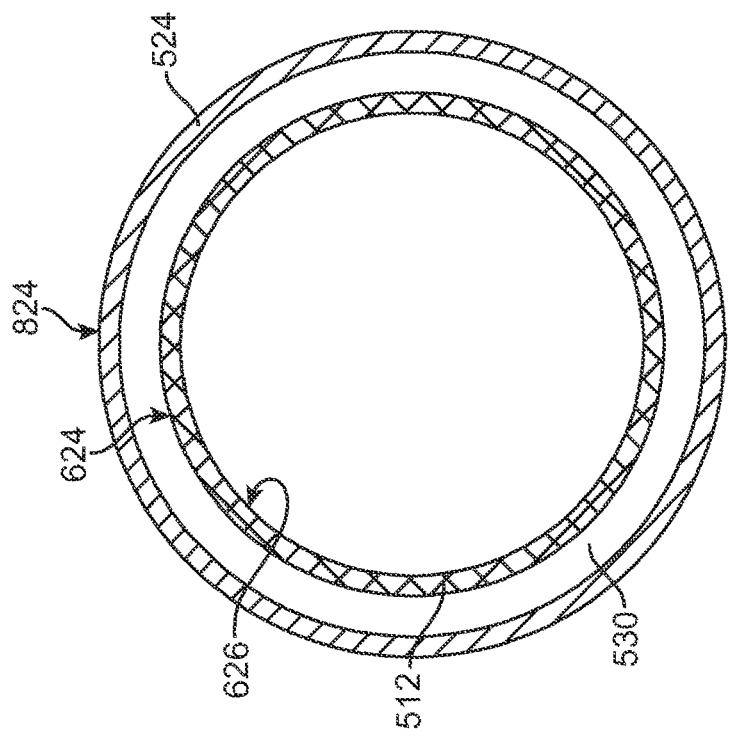
FIG. 24 is a cross-sectional view of FIG. 21 along line C-C.

FIGS. 19-21 further illustrate an embodiment in which the electrode 1610 includes electrodes and 1620 each include two apertures. FIG. 21 includes cross-sectional lies A-A to G-G corresponding to different cross sectional front views of FIG. 19. FIG. 22 is a cross-sectional view of FIG. 21 along line A-A. As shown in FIG. 22, this section has no insulation member 530. Rather, this section includes the proximal end 514 of the first electrode 510. FIG. 23 is a cross-sectional view of FIG. 21 along line B-B. As shown in FIGS. 21 and 23, one portion 2101 of the insulation member 530 extends around the outer surface 624 of the distal end 512 of the first electrode having a reduced outer diameter. This portion 2101 of the insulation member 530 forms an outer surface of the probe and is visible to a user. FIG. 24 is a cross-sectional view of FIG. 21 along line C-C. As shown in FIGS. 21 and 24, another portion 2102 of the insulation member 530 is sandwiched between overlapping ends 512 and 524 of respective electrodes 510 and 520.

Figure 25:
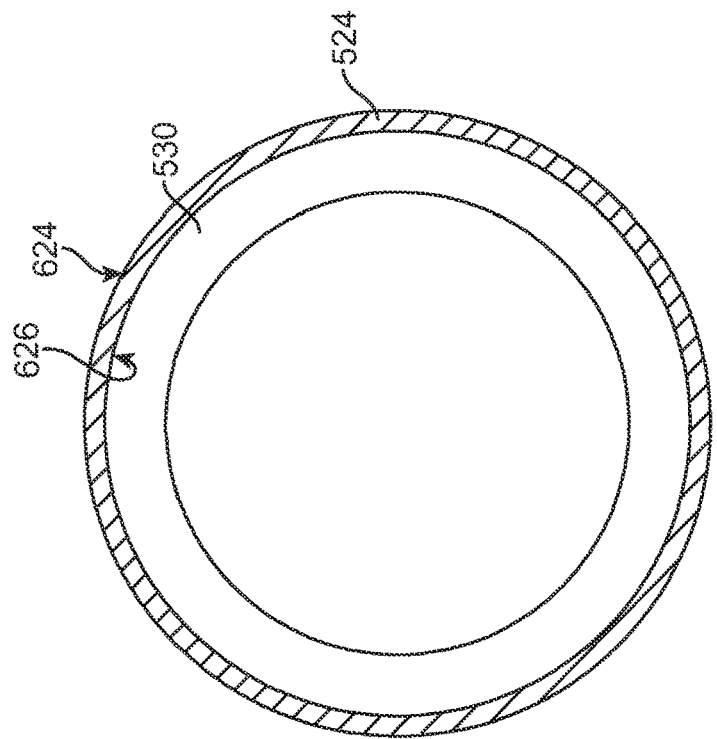
FIG. 25 is a cross-sectional view of FIG. 21 along line D-D.
Figure 27:
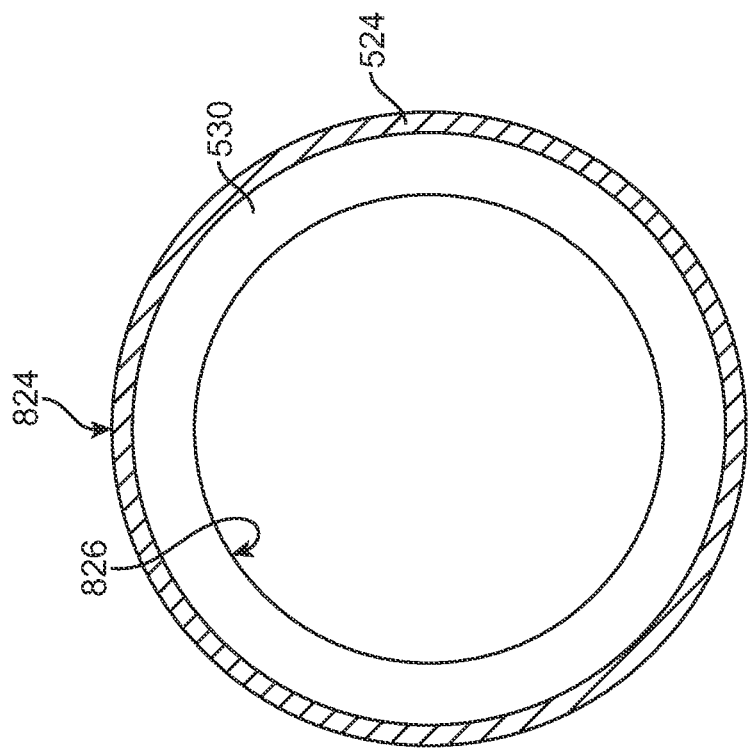
FIG. 27 is a cross-sectional view of FIG. 21 along line F-F of FIG. 21.
Figure 26:
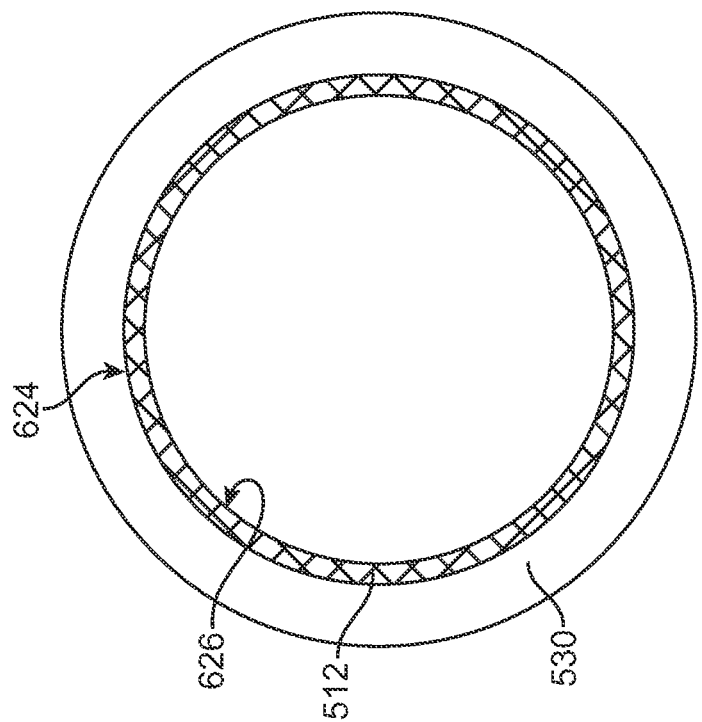
FIG. 26 is a cross-sectional view of FIG. 21 along line E-E.
Figure 28:
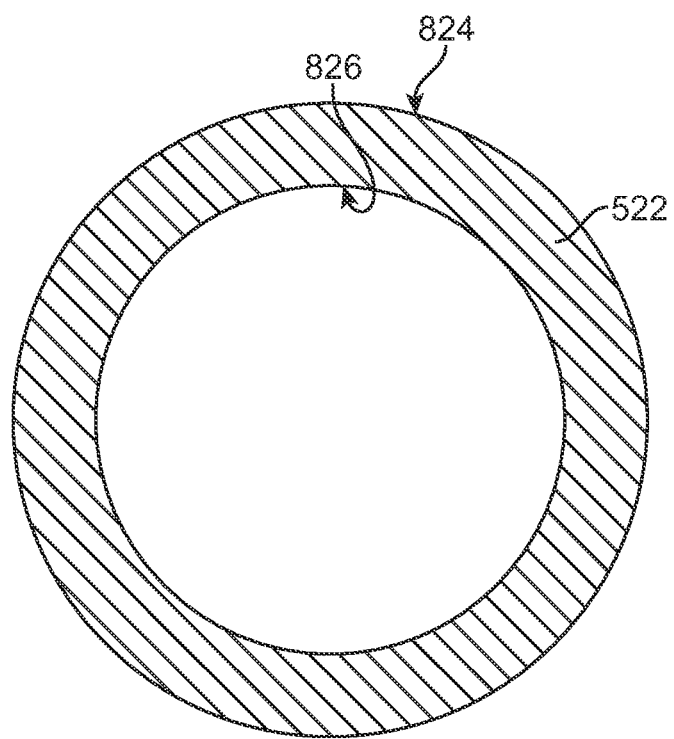
FIG. 28 is a cross-sectional view of FIG. 21 along line G-G.
Figure 29:
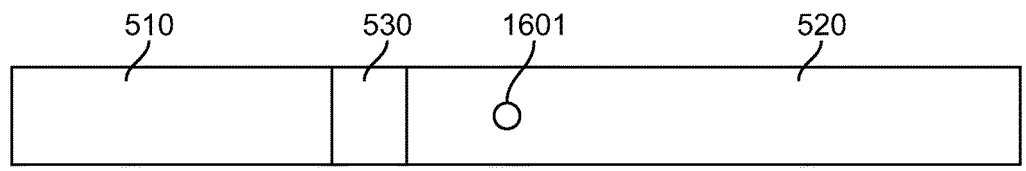
FIG. 29 illustrates an electrode that includes a single circular aperture formed through the wall or body of the electrode according to another embodiment.
Figure 30:
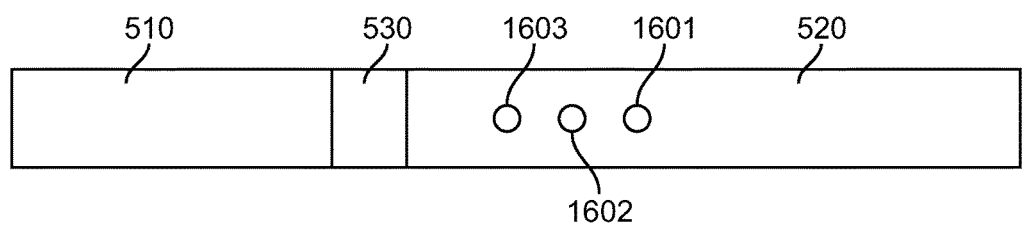
FIG. 30 illustrates an electrode that includes three circular apertures in a linear arrangement and formed through the wall or body of the electrode according to another embodiment.
Figure 31:
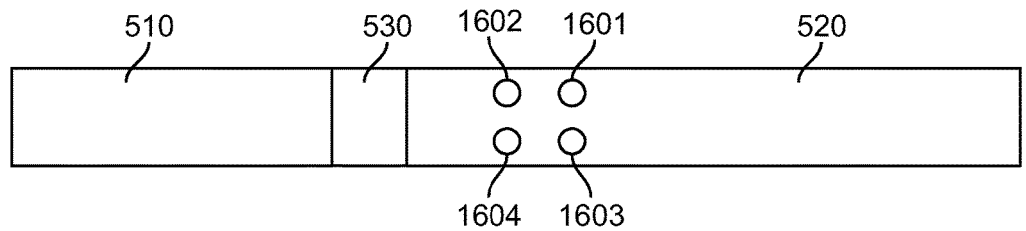
FIG. 31 illustrates an electrode that includes four circular apertures formed through the wall or body of the electrode according to one embodiment.
Figure 32:
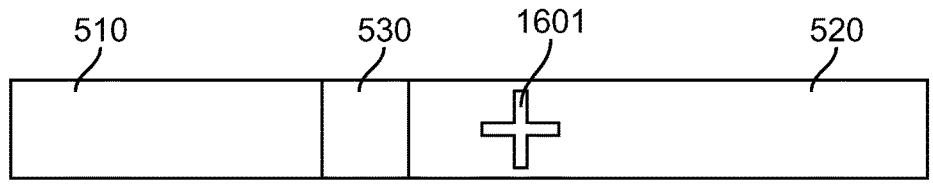
FIG. 32 illustrates an electrode that includes an "X" shaped aperture formed through a wall or body of the electrode according to another embodiment.
Figure 33:
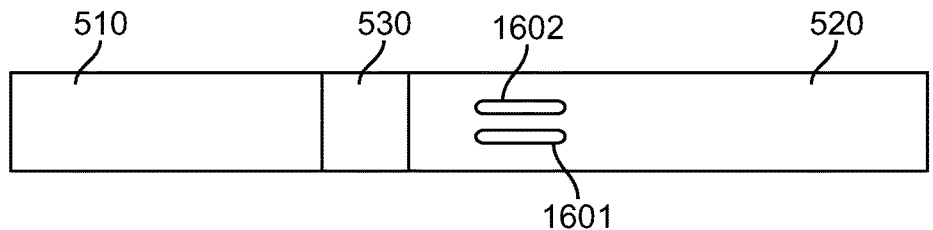
FIG. 33 illustrates an electrode that includes two horizontal slots or elongated apertures formed through a wall or body of the electrode according to another embodiment.
Figure 34:
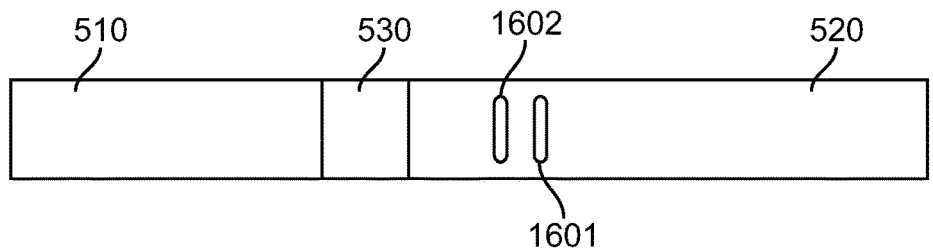
FIG. 34 illustrates an electrode that includes two vertical slots or apertures formed through a wall or body of the electrode according to another embodiment.
Figure 35:
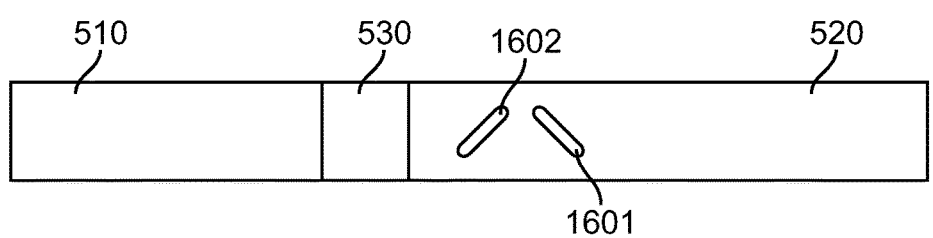
FIG. 35 illustrates an electrode that includes two angled slots formed through a wall or body of the electrode according to another embodiment.
Figure 36:
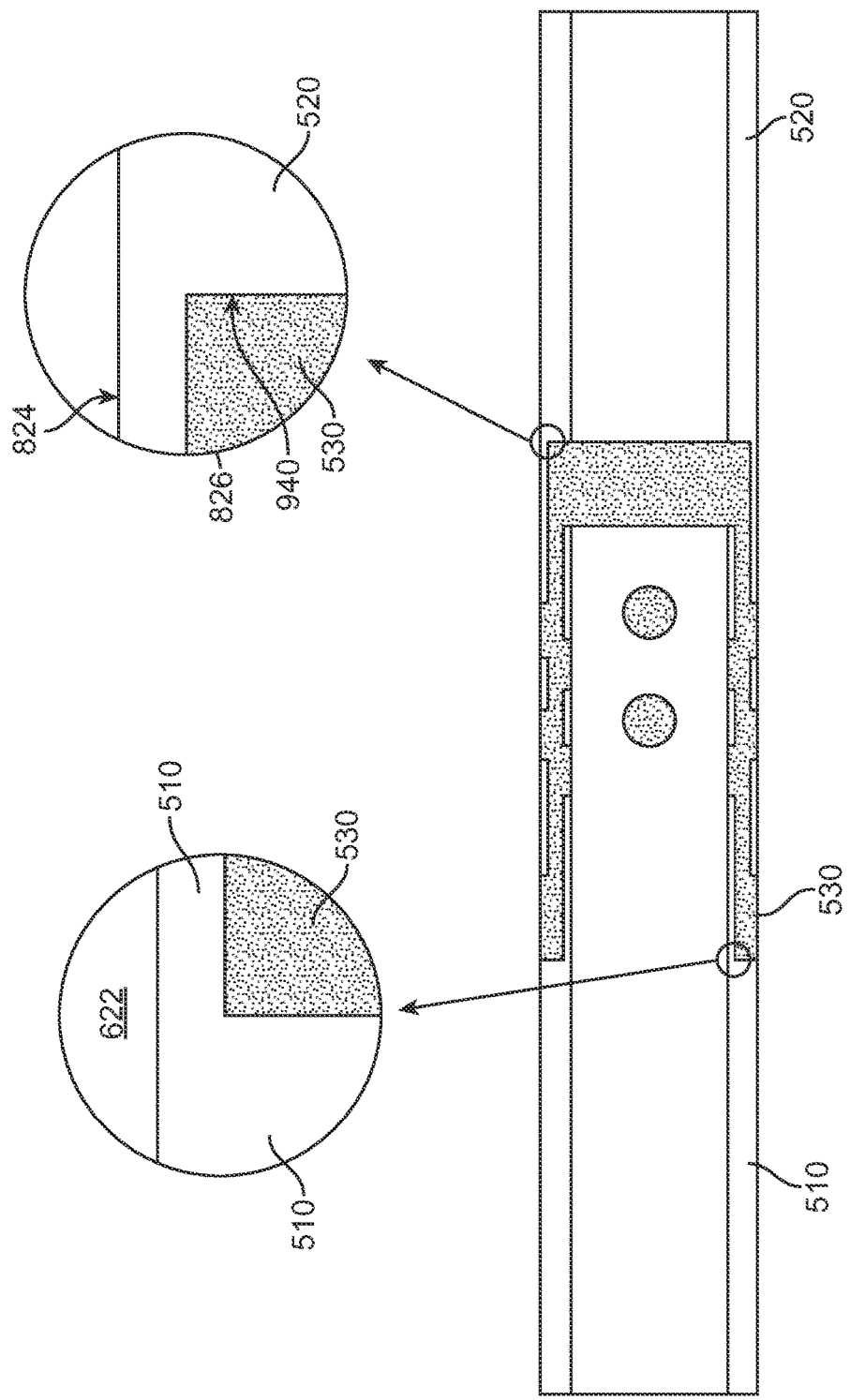
FIG. 36 is a partial cross-sectional side view of an electrosurgical probe according to one embodiment illustrating orthogonal transition edges.

More particularly, the insulation member 530 is between an outer surface 624 of the distal end 512 of the first electrode 510 and an inner surface 826 of the proximal end 524 of the second electrode 520. FIG. 25 is a cross-sectional view of FIG. 21 along line D-D. As shown in FIGS. 21 and 25, a portion 2103 of the insulation member 530 extends along an inner surface 626 of the proximal end 524 of the second electrode 520. FIG. 26 is a cross-sectional front view of FIG. 21 along line E-E. As shown in FIGS. 21 and 36, a portion 2104 of the insulation member 530 extends from an outer surface 624 of the distal end 512 of the first electrode 510 and forms an outer surface of the probe. Thus, this portion 2104 of the insulation member 530 is visible to a user. FIG. 27 is a cross-sectional front view of FIG. 21 along line F-F. As shown in FIGS. 21 and 27, a portion 2105 of the insulation member 530 extends between inner surfaces 826 of the proximal end 524 of the second electrode 520. FIG. 28 is a cross-sectional front view of FIG. 21 along line G-G. As shown in FIGS. 21 and 28, this section has no insulation member 530. Rather, this section includes the proximal end 524 of the second electrode 520.

Other portions of the insulation member 530 may extend between or contact various surfaces and have various thicknesses depending on the configuration that is utilized. Further, different portions of the insulation member 530 can have different thicknesses, extend to different lengths, contact different electrode surfaces, and contact different numbers of electrode surfaces. Thus, FIGS. 16A-28 are provided to generally illustrate that the insulation member 530, whether formed by injection or other methods, can fill spaces of various shapes and sizes depending on, for example, the shape and location of the distal end 512 of the first electrode 510, the proximal end 524 of the second electrode 520, and the shape, number and location of any apertures formed in the first electrode 510 and/or the second electrode 520.

Further, as shown in FIGS. 29-35, one or more electrodes can have various numbers, shapes, sizes and arrangements of apertures. For example, an electrode can include various numbers and size of circular apertures (1601, 1602, 1603, and 1604 FIGS. 29-31), "X" or cross-like apertures 1601 having both vertical and horizontal components (FIG. 32), and lateral or horizontal (1601 and 1602 of FIG. 33), vertical (1601 and 1602 of FIG. 34) or angled apertures (1601 and 1602 of FIG. 35). The size, shape, design and position of the apertures may provide additional strength to absorb tensile and torsion forces, prevent the two electrodes 510 and 520 from pulling apart from each other and provide additional optional injection ports.

Thus, specification sections describing and illustrating an electrode having two circular apertures are provided for purposes of explanation and illustration since various numbers, shapes and sizes of apertures can be used. Further, although FIGS. 29-35 illustrate various numbers, shapes, sizes and arrangements of apertures formed through a wall of a second electrode 520, the same and other aperture configurations can also be formed through the first electrode 510. Additionally, the aperture configuration of the first and second electrodes 510 and 520 can be symmetrical or asymmetrical. For example, the first and second electrodes 510 and 520 can have the same number of apertures, different numbers of apertures, the same aperture shapes and sizes, and different apertures shapes and sizes, the same aperture arrangements or different aperture arrangements.

Figure 37:
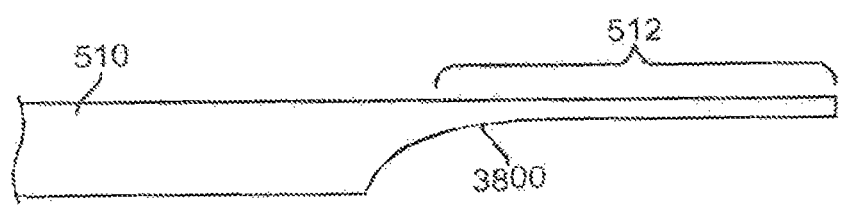
FIG. 37 is a partial cross-sectional side view of an end of an electrode having an arcuate inner surface according to one embodiment.

FIG. 36 further illustrates orthogonal transition areas, i.e., the step-down transition at the edge 640 of the first electrode 510 and the step-up transition at the edge 940 of the second electrode 520. Referring to FIG. 37, in an alternative embodiment, an edge of an electrode can be shaped or formed so that the insulation material 1110 assumes the shape of the shaped edge rather than an orthogonal shape. Shaping the transition areas provides additional strength to withstand larger flex, torque and tensile forces.

Figure 38:
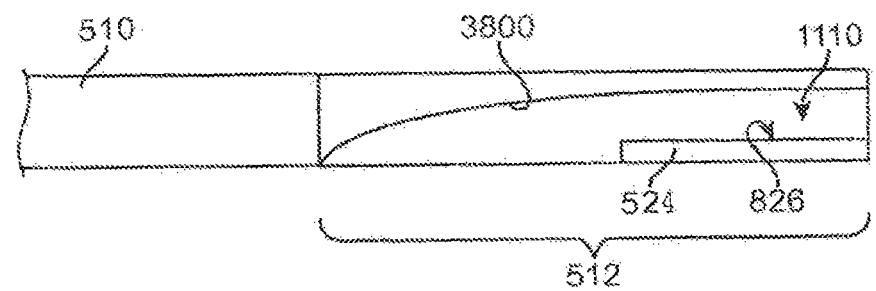
FIG. 38 illustrates an insulation member having a shape corresponding to the arcuate inner surface shown in FIG. 37.
Figure 39:
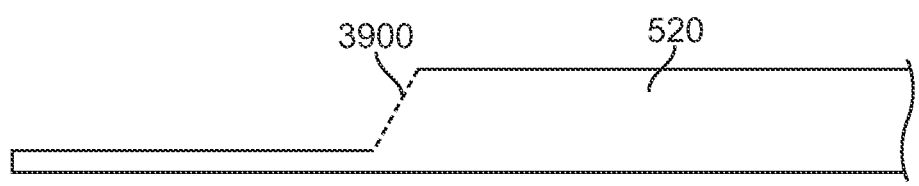
FIG. 39 is a partial cross-sectional side view of an end of an electrode having an angled inner surface according to one embodiment.
Figure 40:
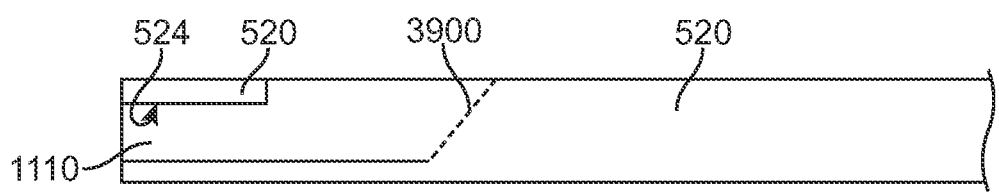
FIG. 40 illustrates an insulation member having a shape corresponding to the angled inner surface shown in FIG. 39.

For example, as shown in FIG. 38, a transition edge 3800 of an electrode, such as the first electrode 510, can have an arcuate shape so that the insulation material 1110 has corresponding arcuate shape. As a further example, referring to FIG. 39, a transition edge 3900 of an electrode, such as the second electrode 520, can be angled so that the insulation material 1110 has a corresponding angled shape as shown in FIG. 40. Edges can also have other transition shapes, such as a radius, a chamfer, etc.

Figure 41:
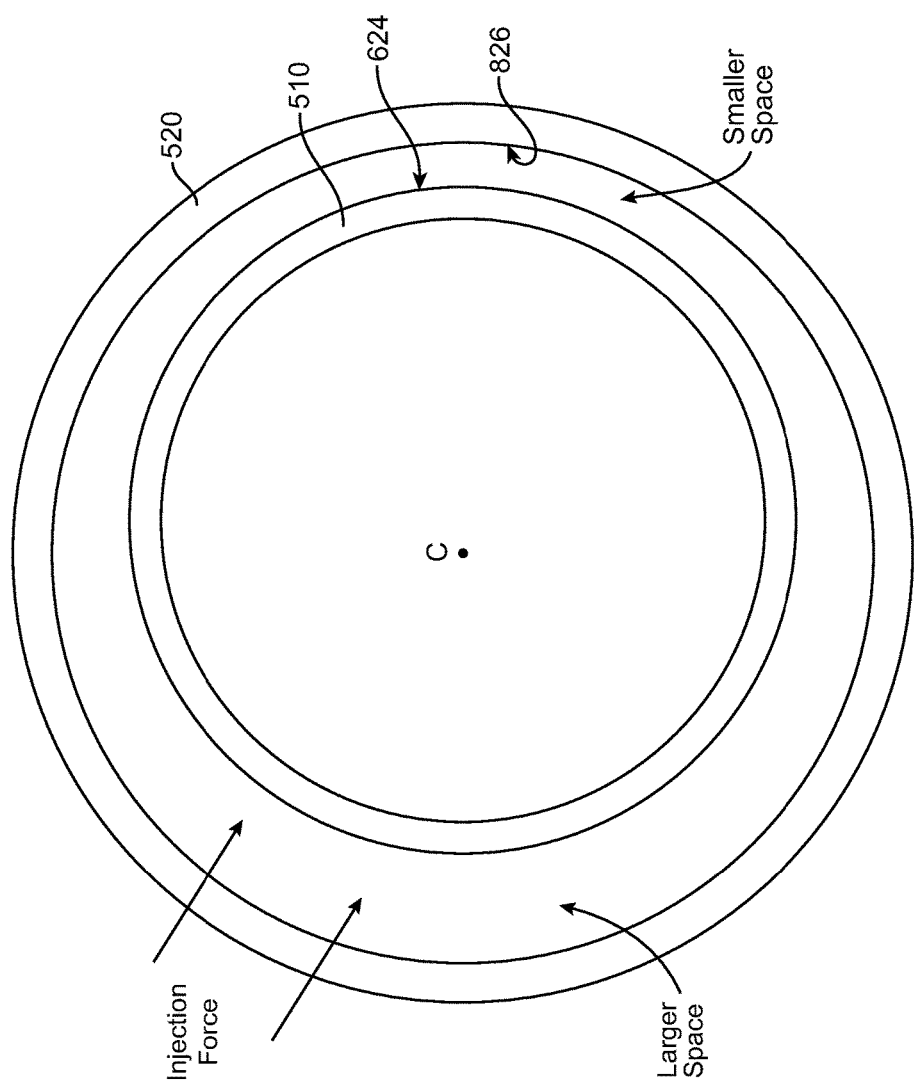
FIG. 41 illustrates an injection force moving an electrode off-center.

Referring to FIG. 41, in embodiments using injection, there may be cases when injection of material 1110 causes the distal end 512 of the first electrode 510 to move off center (C). As a result, the sizes of the space between the outer surface 624 of the distal end 512 of the first electrode 510 and the inner surface 826 of the bored proximal end 524 of the second electrode 520 may vary. For example, as a result of the injection force moving the distal end 512 of the first electrode 510, a larger space is generated in one area, and a smaller space is generated in another area. While this may be acceptable in some situations, reducing the size of the gap between the electrodes 510 and 520 increases the possibility of an electrical short.

Figure 42:
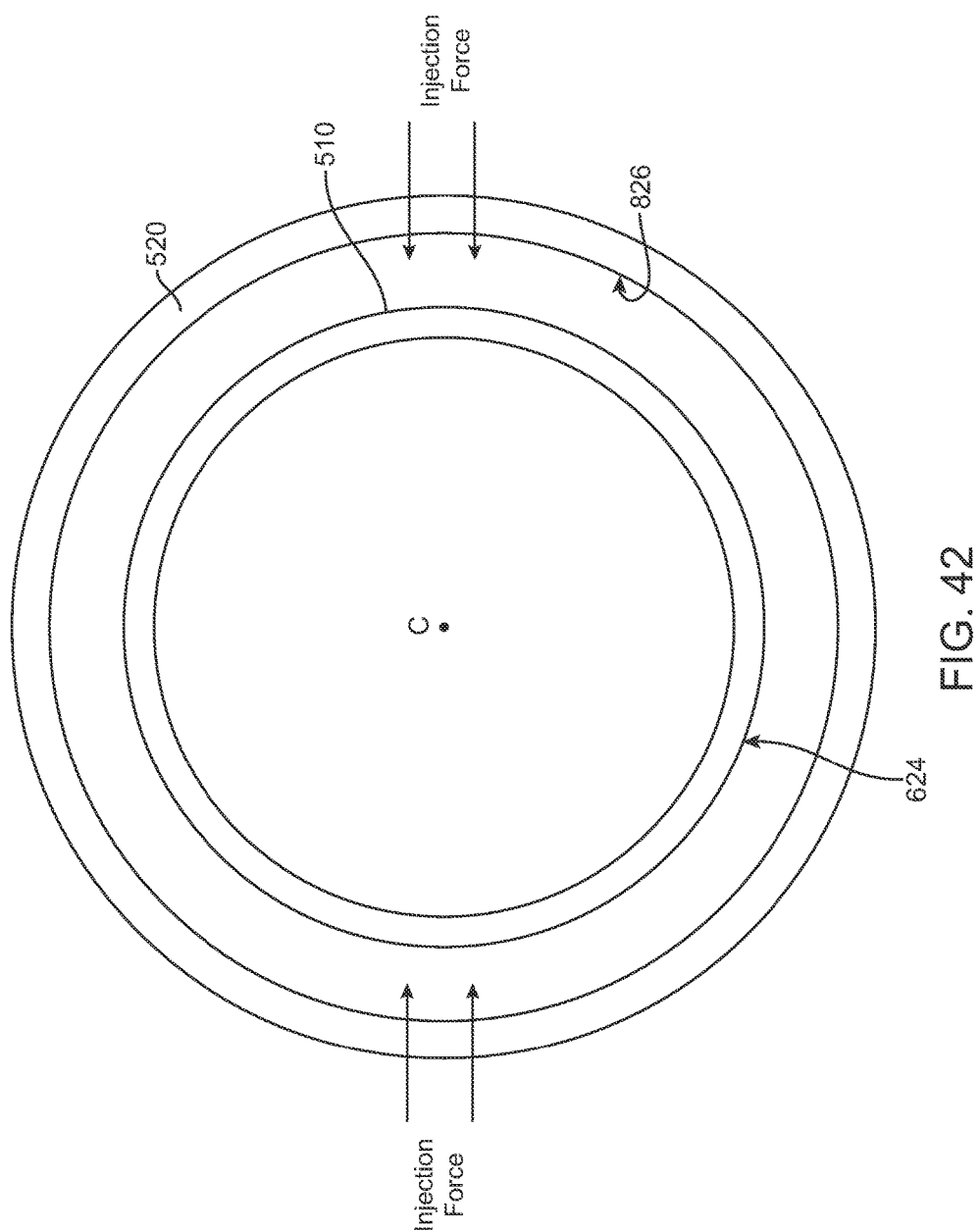
FIG. 42 illustrates a method of applying balanced injection forces according to one embodiment.

Referring to FIG. 42, it may be possible to reduce the possibility of or prevent a short between the electrodes 510 and 520 by injecting insulation material 1110 into different sides of the probe at the same time. Thus, balanced, simultaneous injection forces may counteract so that the distal end 512 of the first electrode 510 does not move or moves by only a small amount. Further, if necessary injection be performed through apertures formed in the top and bottom of an electrode.

Figure 43:
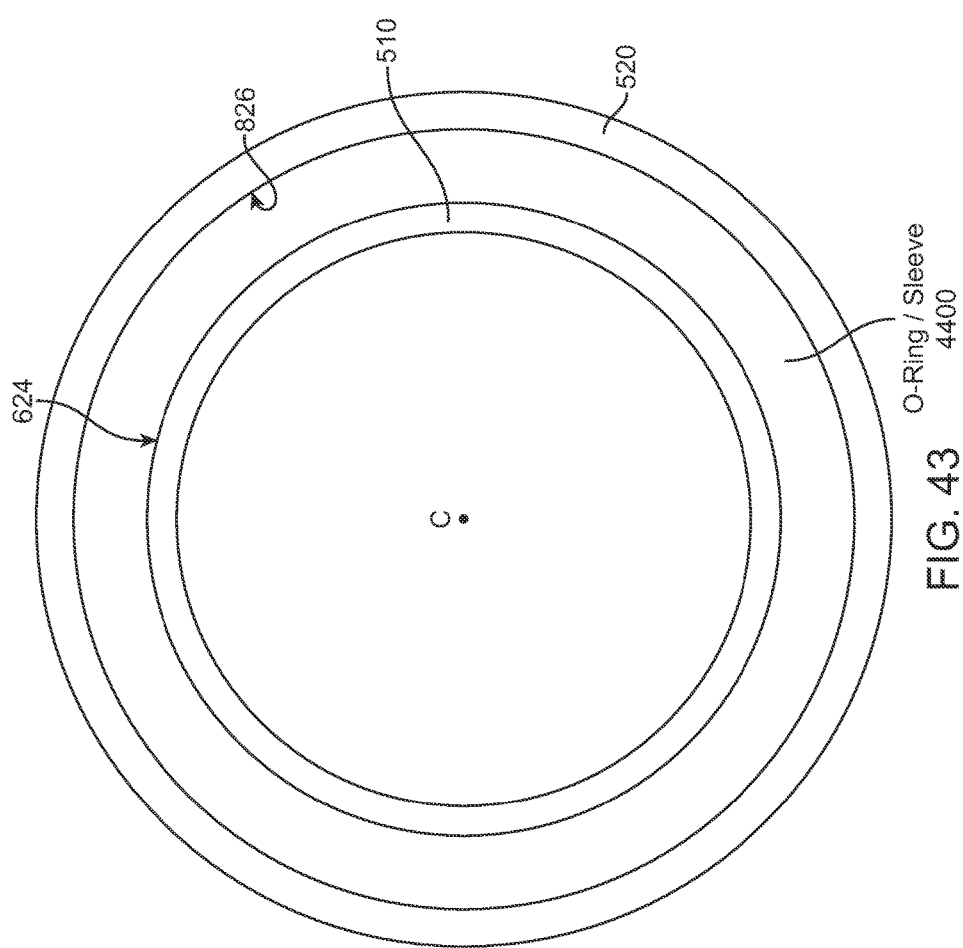
FIG. 43 illustrates an insulation support sleeve or ring disposed between first and second electrodes to counter injection forces so that the first electrode remains on center according to another embodiment.
Figure 44:
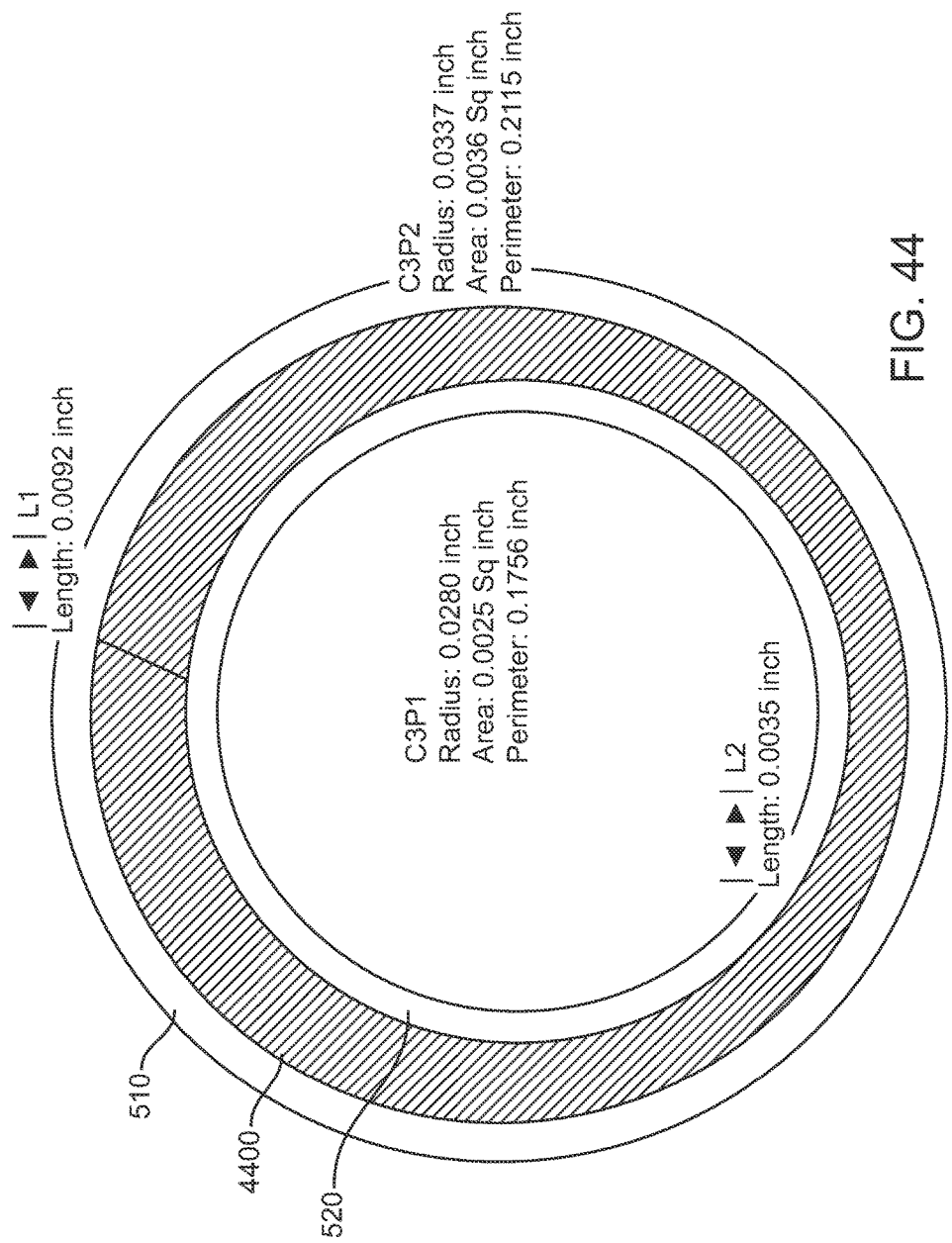
FIG. 44 further illustrates an insulation support sleeve or ring as shown in FIG. 43.

In a further alternative embodiment, referring to FIGS. 43 and 44, an injection force can be countered by use of an insulation sleeve or O-ring 4400 that is positioned between the outer surface 624 of the distal end 512 of the first electrode 510 and an inner surface 826 of the proximal end 524 of the second electrode 520. Suitable insulation O-rings or sleeves 4400 can be composed of PEEK or other suitable non-conductive materials.

During manufacture, the sleeve 4400 can be applied over the distal end 512 of the first electrode 510, and this assembly is then inserted into the lumen of the proximal end 524 of the second electrode 520. Alternatively, the sleeve 4400 can be inserted into the lumen of the second electrode 520 so that the outer surface of the sleeve 4400 is in frictional engagement with the inner surface 826 of the proximal end 524 of the second electrode 520. The distal end 512 of the first electrode 510 can then be inserted into the lumen of the second electrode 520 and through the aperture of the sleeve 4400. Material 1110 can then be injected, e.g., through an aperture formed through a wall of an electrode or through a space between edge or ends of an electrode, and the O-ring or sleeve 4400 can absorb forces and maintain the center arrangement or reduce displacement of an electrode.

Although particular embodiments have been shown and described, it should be understood that the above description is not intended to limit the scope of embodiments since various changes and modifications may be made without departing from the scope of the claims. For example, persons skilled in the art will appreciate that the features disclosed herein can be applied to various bipolar electrosurgical probes. Additionally, in embodiments that utilize apertures formed through the bodies of electrodes, various numbers, shapes, sizes and arrangements of apertures can be utilized as needed. Further, embodiments can be implemented using injection or micro-molding, placing or gluing an insulation material in place, or other suitable methods and devices. Thus, embodiments are intended to cover alternatives, modifications, and equivalents that fall within the scope of the claims.

What is claimed is:

1. A bipolar electrosurgical probe including an elongated probe shaft, the probe being configured for applying electrical energy to tissue, the probe comprising:
   a first tubular electrode carried by the probe shaft and having a distal end;
   a second tubular electrode carried by the probe shaft and having a proximal end; and
   an insulation member, wherein at least a portion of the insulation member is disposed between overlapping ends of the first and second tubular electrodes,
wherein only the distal end of the first electrode and only the proximal end of the second electrode overlap one another,
   wherein the distal end of the first electrode defines at least one aperture extending through a solid continuous first side wall of the first electrode, and
wherein a thickness of the first side wall at the distal end of the first electrode is less than a thickness of the first side wall at a proximal end of the first electrode, and a thickness of a solid continuous second side wall of the second electrode at the proximal end of the second electrode is less than a thickness of the second side wall at a distal end of the second electrode.

2. The probe of claim 1, wherein the distal end of the first electrode defines multiple apertures.

3. The probe of claim 1, wherein the insulation member extends into the at least one aperture of the first electrode.

4. The probe of claim 1, wherein the proximal end of the second electrode defines at least one aperture extending through a solid second wall of the second electrode.

5. The probe of claim 4, wherein the proximal end of the second electrode defines multiple apertures.

6. The probe of claim 4, wherein the insulation member extends into the at least one aperture of the second electrode.

7. The probe of claim 1, wherein the proximal end of the second electrode defines at least one aperture extending through the second side wall, and wherein the insulation member extends into the at least one aperture of the first electrode and the at least one aperture of the second electrode.

8. The probe of claim 1, wherein the distal end of the first electrode is disposed inside a lumen defined by the second side wall of the second electrode at the proximal end of the second electrode.

9. The probe of claim 1, wherein a width of a lumen defined by the first side wall at the distal end of the first electrode is less than a width of a lumen defined by the first side wall at a proximal end of the first electrode, or wherein a width of a lumen defined by the second side wall at the proximal end of the second electrode is greater than a width of a lumen defined by the second side wall at a distal end of the second electrode.

10. The probe of claim 1, wherein the insulation member can assume a shape of a space between a surface of the distal end of the first electrode and a surface of the proximal end of the second electrode.

11. The probe of claim 1, wherein an outer surface of the first electrode is substantially continuous with an outer surface of the second electrode.

12. A bipolar electrosurgical probe including an elongated probe shaft, the probe being configured for applying electrical energy to tissue, the probe comprising:
   a first tubular electrode carried by the probe shaft and having a distal end;
   a second tubular electrode carried by the probe shaft and having a proximal end; and
   an insulation member, wherein at least a portion of the insulation member is disposed between overlapping ends of the first and second tubular electrodes,
wherein only the distal end of the first electrode and only the proximal end of the second electrode overlap one another,
   wherein the distal end of the first electrode and the proximal end of the second electrode have a non-orthogonal shaped cross-section, and the insulation member has a corresponding non-orthogonal shaped cross-section, and
wherein a thickness of a solid continuous first side wall at the distal end of the first electrode is less than a thickness of the first side wall at a proximal end of the first electrode, and a thickness of a solid continuous second side wall of the of the second electrode at the proximal end of the second electrode is less than a thickness of the second side wall at a distal end of the second electrode.

13. The probe of claim 12, wherein portions of the insulation member form an outer surface of the probe.

14. The probe of claim 12, wherein the distal end of the first electrode defines at least one aperture extending through the first side wall of the first electrode.

15. The probe of claim 14, wherein the insulation member extends into the at least one aperture of the first electrode.

16. A bipolar electrosurgical probe including an elongated probe shaft, the probe being configured to apply electrical energy to tissue, the probe comprising:
   a first cylindrical electrode carried by the probe shaft and having proximal and distal ends;
   a second cylindrical electrode carried by the probe shaft and having proximal and distal ends, wherein the second cylindrical electrode is tubular; and
   an insulation member disposed between the first and second cylindrical electrodes,
   wherein only the distal end of the first electrode and only the proximal end of the second electrode overlap one another,
   wherein a first portion of the insulation member is disposed between an outer surface of the distal end of the first electrode and an inner surface of the proximal end of the second electrode, and a second portion of the insulation member forms part of an outer surface of the probe, wherein the first portion of the insulation member is between concentric walls of the first and second electrodes, and
   wherein a thickness of a solid continuous first side wall at the distal end of the first electrode is less than a thickness of the first side wall at a proximal end of the first electrode, and a thickness of a solid continuous second side wall of the of the second electrode at the proximal end of the second electrode is less than a thickness of the second side wall at a distal end of the second electrode.

17. The probe of claim 16, the insulation member comprising a material injected into a space between the first and second electrodes.

18. The probe of claim 16 wherein the first cylindrical electrode comprises a first solid cylindrical wall and the distal end of the first cylindrical electrode defines at least one aperture formed in a first solid cylindrical wall, and wherein the insulation member extends into the at least one aperture of the first cylindrical electrode.

19. The probe of claim 16 wherein the second cylindrical electrode comprises a second solid cylindrical wall and the proximal end of the second cylindrical electrode defines at least one aperture formed in the second solid cylindrical wall, and wherein the insulation member extends into the at least one aperture of the second cylindrical electrode.

20. The probe of claim 16 wherein the first cylindrical electrode comprises a first solid cylindrical wall and the distal end of the first cylindrical electrode defines at least one aperture formed in a first solid cylindrical wall, wherein the insulation member extends into the at least one aperture of the first cylindrical electrode, wherein the second cylindrical electrode comprises a second solid cylindrical wall and the proximal end of the second cylindrical electrode defines at least one aperture formed in the second solid cylindrical wall, and wherein the insulation member extends into the at least one aperture of the second cylindrical electrode.

21. A bipolar electrosurgical probe including an elongated probe shaft, the probe being configured to apply electrical energy to tissue, the probe comprising:

a first cylindrical electrode carried by the probe shaft and having proximal and distal ends;

a second cylindrical electrode carried by the probe shaft and having proximal and distal ends; and a tubular insulation member disposed between the first and second cylindrical electrodes, wherein only the distal end of the first electrode and only the proximal end of the second electrode overlap one another, wherein a first portion of the insulation member is disposed between an outer surface of the distal end of the first electrode and an inner surface of the proximal end of the second electrode, and a second portion of the insulation member forms part of an outer surface of the probe, wherein the first portion of the insulation member is between concentric walls of the first and second electrodes, and wherein a thickness of a solid continuous first side wall at the distal end of the first electrode is less than a thickness of the first side wall at a proximal end of the first electrode, and a thickness of a solid continuous second side wall of the of the second electrode at the proximal end of the second electrode is less than a thickness of the second side wall at a distal end of the second electrode.

* * * * *